United States Patent
Bettuchi

(10) Patent No.: US 8,424,742 B2
(45) Date of Patent: *Apr. 23, 2013

(54) SUPPORT STRUCTURES AND METHODS OF USING THE SAME

(75) Inventor: Michael J. Bettuchi, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/076,550

(22) Filed: Mar. 31, 2011

(65) Prior Publication Data
US 2011/0230901 A1 Sep. 22, 2011

Related U.S. Application Data

(62) Division of application No. 11/241,267, filed on Sep. 30, 2005, now Pat. No. 7,938,307.

(60) Provisional application No. 60/620,066, filed on Oct. 18, 2004, provisional application No. 60/620,065, filed on Oct. 18, 2004.

(51) Int. Cl.
*A61B 17/10* (2006.01)
*A61B 17/04* (2006.01)
*A61B 17/08* (2006.01)
*A61D 1/00* (2006.01)

(52) U.S. Cl.
USPC ..................... 227/179.1; 606/219

(58) Field of Classification Search .... 227/175.1–182.1, 227/19
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 4,347,847 A | 9/1982 | Usher |
| 4,354,628 A | 10/1982 | Green |
| 4,452,245 A | 6/1984 | Usher |
| 4,603,693 A | 8/1986 | Conta et al. |
| 4,605,730 A | 8/1986 | Shalaby et al. |

(Continued)

FOREIGN PATENT DOCUMENTS

| | | |
|---|---|---|
| DE | 1 99 24 311 A1 | 11/2000 |
| DE | 199 24 311 A1 | 11/2000 |

(Continued)

OTHER PUBLICATIONS

International Search Report corresponding to European Application No. EP 06 00 4598, completed on Jun. 22, 2006; 2 pages.

(Continued)

*Primary Examiner* — Robert Long

(57) ABSTRACT

According to an aspect of the present disclosure, an apparatus for forming an anastomosis between adjacent intestinal sections of tissue is provided. The apparatus includes an anastomosis device having an anvil and a tubular body portion, wherein the anvil is selectively attachable to the tubular body portion by a shaft; and a support structure for deposition between the intestinal sections of tissue. The support structure includes a body defining an aperture therein for receiving the shaft. The body has an outer terminal edge. The support structure includes at least one layer of expandable material disposed at the outer terminal edge of the body.

12 Claims, 14 Drawing Sheets

U.S. PATENT DOCUMENTS

| | | |
|---|---|---|
| 4,655,221 A | 4/1987 | Devereux |
| 4,703,887 A * | 11/1987 | Clanton et al. .................. 227/19 |
| 4,834,090 A | 5/1989 | Moore |
| 4,838,884 A | 6/1989 | Dumican et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,261,920 A * | 11/1993 | Main et al. .................... 606/153 |
| 5,263,629 A | 11/1993 | Trumbull et al. |
| 5,309,927 A * | 5/1994 | Welch .......................... 128/898 |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,735,833 A | 4/1998 | Olson |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,503,259 B2 * | 1/2003 | Huxel et al. .................. 606/153 |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,769,590 B2 * | 8/2004 | Vresh et al. .................... 227/19 |
| 6,773,458 B1 | 8/2004 | Brauker et al. |
| 6,927,315 B1 | 8/2005 | Heinecke et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,238,195 B2 | 7/2007 | Viola |
| 7,399,305 B2 * | 7/2008 | Csiky et al. .................. 606/139 |
| 7,434,717 B2 | 10/2008 | Shelton, IV et al. |
| 7,438,209 B1 | 10/2008 | Hess et al. |
| 7,455,682 B2 | 11/2008 | Viola |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,669,747 B2 | 3/2010 | Weisenburgh, II et al. |
| 7,699,204 B2 | 4/2010 | Viola |
| 7,744,627 B2 | 6/2010 | Orban, III et al. |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,909,224 B2 | 3/2011 | Prommersberger |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0067454 A1 * | 3/2005 | Vresh et al. .................... 227/19 |
| 2005/0070929 A1 | 3/2005 | Dalessandro et al. |
| 2005/0118435 A1 | 6/2005 | DeLucia et al. |
| 2005/0143756 A1 | 6/2005 | Jankowski |

| | | | | | | |
|---|---|---|---|---|---|---|
| 2005/0149073 | A1 | 7/2005 | Arani et al. | 2011/0024481 A1 | 2/2011 | Bettuchi et al. |
| 2005/0228446 | A1 | 10/2005 | Mooradian et al. | 2011/0036889 A1 | 2/2011 | Heinrich et al. |
| 2005/0245965 | A1 | 11/2005 | Orban et al. | 2011/0036894 A1 | 2/2011 | Bettuchi |
| 2006/0004407 | A1 | 1/2006 | Hiles et al. | 2011/0042442 A1 | 2/2011 | Viola et al. |
| 2006/0085032 | A1 | 4/2006 | Viola | 2011/0046650 A1 | 2/2011 | Bettuchi |
| 2006/0085034 | A1 | 4/2006 | Bettuchi | 2011/0057016 A1 | 3/2011 | Bettuchi |
| 2006/0135992 | A1 | 6/2006 | Bettuchi et al. | | | |
| 2006/0173470 | A1 | 8/2006 | Oray et al. | | | |

FOREIGN PATENT DOCUMENTS

| | | |
|---|---|---|
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 520 525 A1 | 4/2005 |
| EP | 1 621 141 A21 | 2/2006 |
| EP | 1 702 570 A1 | 9/2006 |
| EP | 1 759 640 A2 | 3/2007 |
| EP | 1 815 804 A2 | 8/2007 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 198 787 A1 | 6/2010 |
| EP | 2 236 098 A2 | 10/2010 |
| JP | 06327683 A | 11/1994 |
| JP | 2000-166933 | 6/2000 |
| WO | WO 90/05489 A1 | 5/1990 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/0082126 A1 | 10/2003 |
| WO | WO 03/082126 A1 | 10/2003 |
| WO | WO 03/088845 A2 | 10/2003 |
| WO | WO 03/0105698 A2 | 12/2003 |
| WO | WO 03/105698 A2 | 12/2003 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

Additional continued listings:

| | | | |
|---|---|---|---|
| 2006/0178683 A1 | 8/2006 | Shimoji et al. | |
| 2006/0212050 A1 | 9/2006 | D'Agostino et al. | |
| 2006/0271104 A1 | 11/2006 | Viola et al. | |
| 2007/0026031 A1 | 2/2007 | Bauman et al. | |
| 2007/0034669 A1 | 2/2007 | de la Torre et al. | |
| 2007/0049953 A2 | 3/2007 | Shimoji et al. | |
| 2007/0123839 A1 | 5/2007 | Rousseau et al. | |
| 2007/0179528 A1 | 8/2007 | Soltz et al. | |
| 2007/0203509 A1 | 8/2007 | Bettuchi | |
| 2007/0203510 A1 | 8/2007 | Bettuchi | |
| 2007/0246505 A1 | 10/2007 | Pace-Floridia et al. | |
| 2008/0029570 A1 | 2/2008 | Shelton et al. | |
| 2008/0082126 A1 | 4/2008 | Murray et al. | |
| 2008/0110959 A1 | 5/2008 | Orban et al. | |
| 2008/0125812 A1 | 5/2008 | Zubik et al. | |
| 2008/0140115 A1 | 6/2008 | Stopek | |
| 2008/0161831 A1 | 7/2008 | Bauman et al. | |
| 2008/0161832 A1 | 7/2008 | Bauman et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0290134 A1 | 11/2008 | Bettuchi et al. | |
| 2008/0308608 A1 | 12/2008 | Prommersberger | |
| 2008/0314960 A1 | 12/2008 | Marczyk et al. | |
| 2009/0001121 A1 | 1/2009 | Hess et al. | |
| 2009/0001122 A1 | 1/2009 | Prommersberger et al. | |
| 2009/0001123 A1 | 1/2009 | Morgan et al. | |
| 2009/0001124 A1 | 1/2009 | Hess et al. | |
| 2009/0001125 A1 | 1/2009 | Hess et al. | |
| 2009/0001126 A1 | 1/2009 | Hess et al. | |
| 2009/0001128 A1 | 1/2009 | Weisenburgh, II et al. | |
| 2009/0001130 A1 | 1/2009 | Hess et al. | |
| 2009/0005808 A1 | 1/2009 | Hess et al. | |
| 2009/0030452 A1 | 1/2009 | Bauman et al. | |
| 2009/0043334 A1 | 2/2009 | Bauman et al. | |
| 2009/0076510 A1 | 3/2009 | Bell et al. | |
| 2009/0076528 A1 | 3/2009 | Sgro | |
| 2009/0078739 A1 | 3/2009 | Viola | |
| 2009/0095791 A1 | 4/2009 | Eskaros et al. | |
| 2009/0095792 A1 | 4/2009 | Bettuchi | |
| 2009/0120994 A1 | 5/2009 | Murray et al. | |
| 2009/0134200 A1 | 5/2009 | Tarinelli et al. | |
| 2009/0206125 A1 | 8/2009 | Huitema et al. | |
| 2009/0206126 A1 | 8/2009 | Huitema et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0218384 A1 | 9/2009 | Aranyi | |
| 2009/0277947 A1 | 11/2009 | Viola | |
| 2009/0287230 A1 | 11/2009 | D'Agostino et al. | |
| 2010/0012704 A1 | 1/2010 | Tarinelli Racenet et al. | |
| 2010/0065606 A1 | 3/2010 | Stopek | |
| 2010/0065607 A1 | 3/2010 | Orban, III et al. | |
| 2010/0072254 A1 | 3/2010 | Aranyi et al. | |
| 2010/0147921 A1 | 6/2010 | Olson | |
| 2010/0147922 A1 | 6/2010 | Olson | |
| 2010/0147923 A1 | 6/2010 | D'Agostino et al. | |
| 2010/0213239 A1* | 8/2010 | Rebuffat et al. | 227/180.1 |
| 2010/0230466 A1 | 9/2010 | Criscuolo et al. | |
| 2010/0243707 A1 | 9/2010 | Olson et al. | |
| 2010/0243708 A1 | 9/2010 | Aranyi et al. | |
| 2010/0243711 A1 | 9/2010 | Olson et al. | |
| 2010/0249805 A1 | 9/2010 | Olson et al. | |
| 2010/0264195 A1 | 10/2010 | Bettuchi | |
| 2010/0282815 A1 | 11/2010 | Bettuchi et al. | |
| 2011/0024476 A1 | 2/2011 | Bettuchi et al. | |

OTHER PUBLICATIONS

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

International Search Report corresponding to European Application No. EP 08 25 1989.3, completed on Mar. 24, 2010 and mailed on Mar. 24, 2010; 3 pages.

International Search Report corresponding to European Application No. EP 05 80 4382.9, completed on Oct. 5, 2010 and mailed on Oct. 12, 2010; 3 pages.

International Search Report corresponding to European Application No. EP 10 25 1437.9, completed on Nov. 22, 2010 and mailed on Dec. 16, 2010; 3 pages.

International Search Report corresponding to European Application No. EP 09 25 2897.5, completed on Feb. 7, 2011 and mailed on Feb. 15, 2011; 3 pages.

Extended International Search Report corresponding to European Application No. EP 05022585.3, completed Jan. 25, 2006 and mailed Feb. 3, 2006; 4 pages.

Extended International Search Report corresponding to European Application No. EP 06016962.0, completed Jan. 3, 2007 and mailed Jan. 11, 2007; 6 pages.

International Search Report corresponding to European Application No. PCT/US05/36740, completed Feb. 20, 2007 and mailed Mar. 23, 2007; 8 pages.

International Search Report corresponding to International Application No. PCT/US2008/002981, completed Jun. 9, 2008 and mailed Jun. 26, 2008; 2 pages.

Extended International Search Report corresponding to European Application No. EP 08 25 1779.8, completed Jul. 14, 2008 and mailed Jul. 23, 2008; 5 pages.

International Search Report corresponding to European Application No. EP 10 25 0715.9, completed on Jun. 30, 2010 and mailed on Jul. 20, 2010; 3 pages.

International Search Report corresponding to European Application No. EP 10 25 0642.5, completed on Mar. 25, 2011 and mailed on Apr. 4, 2011; 4 pages.

International Search Report corresponding to European Application No. EP 11 18 8309.6, completed on Dec. 15, 2011 and mailed on Jan. 12, 2012; 3 pages.

International Search Report corresponding to European Application No. EP 12 15 2229.6, completed on Feb. 23, 2012 and mailed on Mar. 1, 2012; 4 pages.

International Search Report corresponding to European Application No. EP 12 15 0511.9, completed on Apr. 16, 2012 and mailed on Apr. 24, 2012; 7 pages.

International Search Report corresponding to European Application No. EP 12 15 2541.4, completed on Apr. 23, 2012 and mailed on May 3, 2012; 10 pages.

International Search Report corresponding to European Application No. EP 12 16 5609.4, completed on Jul. 5, 2012 and mailed on Jul. 13, 2012; 8 pages.

International Search Report corresponding to European Application No. EP 12 15 8861.0, completed on Jul. 17, 2012 and mailed on Jul. 24, 2012; 9 pages.

International Search Report corresponding to European Application No. EP 12 16 5878.5, completed on Jul. 24, 2012 and mailed on Aug. 6, 2012; 8 pages.

International Search Report corresponding to European Application No. EP 05809831.0-1269 mailed May 14, 2012; 10 pages.

* cited by examiner

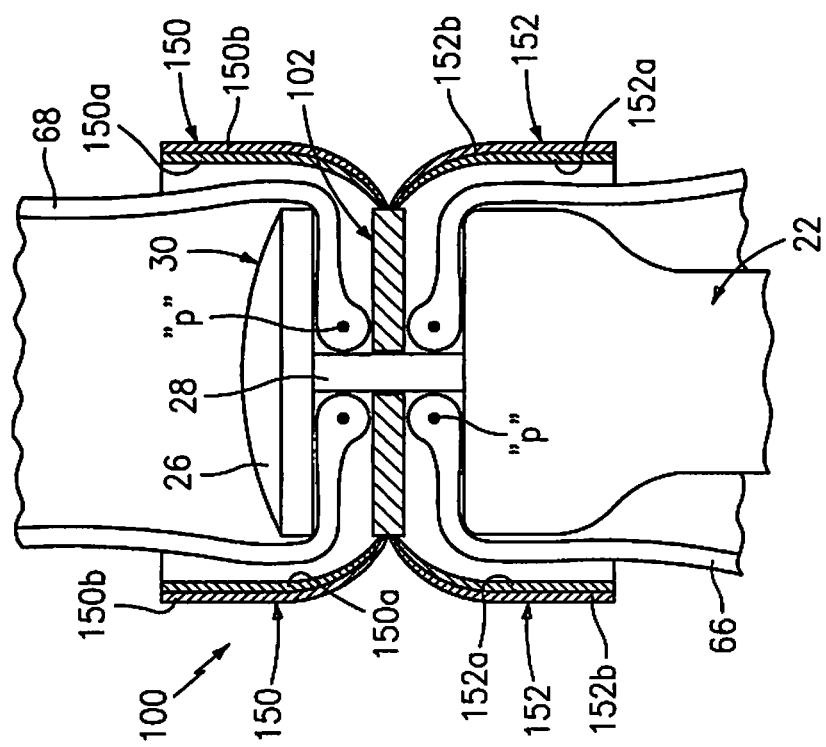
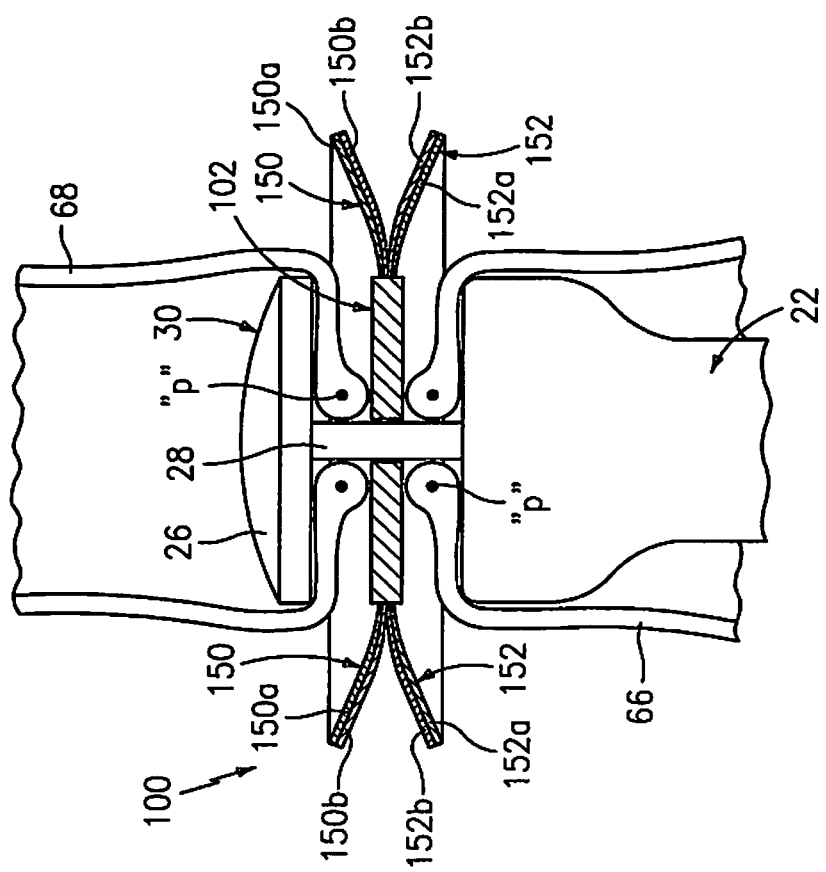

SUPPORT STRUCTURES AND METHODS OF USING THE SAME

CROSS-REFERENCE TO RELATED APPLICATIONS

This application is a divisional of U.S. application Ser. No. 11/241,267 filed Sep. 30, 2005, now U.S. Pat. No. 7,938,307 which claims benefit of application No. 60/620,066 filed Oct. 18, 2004, which claims benefit of application No. 60/620,065 filed Oct. 18, 2004, and the disclosures of each of the above-identified applications are hereby incorporated by reference in their entirety.

BACKGROUND

1. Technical Field

The present disclosure relates to support structures and, more particularly, to annular support structures, gaskets and the like for use in conjunction with stapling devices, for reducing occurrences of leaking, bleeding and/or stricture.

2. Background of Related Art

Staples have traditionally been used to replace suturing when joining or anastomosing various body structures, such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of anastomoses. Linear surgical stapling devices generally include a pair of jaws or finger-like structures between which body tissue to be joined is placed. When the surgical stapling device is actuated and/or "fired", firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such surgical stapling devices are described in U.S. Pat. Nos. 4,354,628, 5,014,899 and 5,040,715, the entirety of each of which is incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples. Examples of such annular surgical stapling devices are described in U.S. Pat. Nos. 5,799,857 and 5,915,616 to Robertson et al., the entirety of each of which is incorporated herein by reference.

For most procedures, the use of bare staples, with the staples in direct contact with the patient's tissue, is generally acceptable. The integrity of the tissue will normally serve to prevent the staples from tearing out of the tissue and compromising the sealing before healing has occurred. However, in some surgical operations, surgical supports, e.g., meshes, are employed by surgeons to bridge, repair and/or reinforce tissue defects with a patient, especially those occurring in the abdominal wall, chest wall, diaphragm and other musculo-aponeurotic areas of the body. Examples of surgical supports are disclosed in U.S. Pat. Nos. 3,054,406, 3,124,136, 4,347, 847, 4,655,221, 4,838,884 and 5,002,551, the entirety of each of which is incorporated herein by reference.

When the staples are applied in surgical procedures utilizing surgical supports (i.e., reinforcing material), the legs of the staple typically pass from the cartridge jaw through a layer of the surgical support, and through the patient's tissue before encountering the anvil jaw. In an alternative procedure, the legs of the staple typically pass from the cartridge jaw through a first layer of the surgical support, then through the patient's tissue, and finally through a second layer of the surgical support before encountering the anvil jaw. With the staples in place, the stapled tissue is clamped between the layers of the surgical support.

While the surgical supports described above are used in conjunction with linear surgical stapling devices, the need exists for annular support structure for use in conjunction with annular or circular surgical stapling devices, for example, an end-to-end anastomosis stapler such as a Model "EEA™" instrument available from United States Surgical, a Division of Tyco Health-Care Group, LP, Norwalk, Conn. and disclosed in U.S. Pat. No. 5,392,979 to Green et al. In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

In addition to the use of surgical staples, biological tissue adhesives have been developed for tissue repair and the creation of anastomoses. Generally, biological adhesives bond separated tissues together to aid in the healing process and to enhance the tissue strength. Such adhesives may be used instead of suturing and stapling, for example, in surgical procedures, for the repair of tissue or the creation of anastomoses.

In addition to the use of biological adhesives, following the formation of the anastomosis, a separate instrument or device is used to apply biological sealants to the outer surface of the anastomosis. Typically, in a separate step, the biological sealants are applied to the outer surface of the anastomosis by spraying on, brushing on, swabbing on, any combinations thereof, or any other method contemplated by those skilled in the art. The biological sealants act to reduce and/or stop the incidents of leakage from the anastomosis.

One possible side effect of any end-to-end bowel anastomosis is its tendency to stenos over time, which stenosis can decrease the diameter of the lumen over time. Accordingly, the need exists for a surgical support structure which operates in conjunction with any end-to-end anastomosis device and assists in maintaining the lumen of the anastomosed bowel or other tubular organ open over time.

The application of suitable biocompatible adhesive offers many advantages to the patient and the surgeon alike, such as, for example, the possible reduction in the number of staples used, immediate sealing of the tissue being treated, a strengthening of the anastomosis, and a reduction in the occurrence of bleeding from the blood vessels, leakage through the tissue joint, and stricture. Moreover, use of biocompatible adhesives tends to minimize foreign body reaction and scarring.

Accordingly, the need exists for an annular support structure which operates in conjunction with any end-to-end, annular or circular stapling device and assists in maintaining the lumen of the anastomosed bowel or other tubular organ patent or open over time.

A need also exists for an annular support structure which operates in conjunction with any end-to-end, annular or circular stapling device to reduce the trauma suffered by the patient, reduce the instances of leakage, reduce the instances of bleeding, and create a relatively strong bond between adjacent body tissues.

A need also exists for an annular support structure configured to provide support to the anastomosed tissue, preferably, distally and/or proximally of the staple line.

SUMMARY

According to an aspect of the present disclosure, an apparatus for forming an anastomosis between adjacent intestinal sections of tissue is provided. The apparatus includes an anastomosis device having an anvil and a tubular body portion, wherein the anvil is selectively attachable to the tubular body portion by a shaft; and a support structure for deposition between the intestinal sections of tissue. The support structure includes a body defining an aperture therein for receiving the shaft. The body has an outer terminal edge. The support structure includes at least one layer of expandable material disposed at the outer terminal edge of the body.

The at least one layer of expandable material may include a first and a second membrane extending radially outward from the outer terminal edge of the body.

The aperture may be defined by an inner terminal edge of the body. The inner terminal edge may be disposed radially inward of staple receiving slots of a staple cartridge assembly disposed in the tubular body.

It is envisioned that each of the first and second membranes is made from a polymeric film, such as, for example, polyethylene. The support structure has an undeployed condition wherein the first and second membranes are rolled-up towards the body, and a deployed condition wherein the first membrane extends in a substantially distal direction from the body and the second membrane extends in a substantially proximal direction from the body.

The apparatus may further include a rip-cord for expanding the first and second membranes. The rip-cord is rolled-up into each of the first and second membranes when the support structure is in the undeployed condition.

Each membrane may include a first inner layer and a second outer layer. The second outer layer of each membrane may swell at a rate greater than the first inner layer. The second outer layers of the first and second membranes are made from a hydrogel. The first inner layer of each of the first and second membranes may be constructed from a substantially non-absorbable material. The first inner layer of each of the first and second membranes may be fabricated from a bio-absorbable mesh fabric.

According to another aspect of the present disclosure, a method of disposing a support structure between adjacent intestinal sections is provided. The method includes the step of providing a circular surgical anastomosis device. The circular surgical anastomosis device includes an anvil assembly having an anvil member and a first shaft; and a tubular body portion having an annular knife operatively disposed therein and a second shaft disposed radially inward of the annular knife, the first shaft of the anvil assembly being selectively attachable to the second shaft of the tubular body.

The method further includes the steps of inserting the anvil assembly into a first intestinal section; inserting the tubular body portion into a second intestinal section; disposing a support structure between the first intestinal section and the second intestinal section, the support structure having at least one layer of expandable material; approximating the anvil assembly and tubular body portion with one another so that an end portion of the first intestinal section, the support structure, and an end portion of the second intestinal section are disposed between the anvil member and the tubular body portion, the support structure being disposed between the first intestinal section and the second intestinal section; firing the surgical anastomosis device to sever the portions of the first and second intestinal sections disposed radially inward of the annular knife, and to touch the portions of the first and second intestinal sections radially outward of the annular knife against the structure; and expanding the at least one layer of expandable material The anvil assembly may include a first shaft and the tubular body portion includes a second shaft disposed radially inward of the annular knife. Desirably, the first shaft of the anvil member is attachable to the second shaft of the tubular body portion. Accordingly, the method may further include the step of attaching the first shaft of the anvil assembly to the second shaft of the tubular body portion prior to the step of approximating the anvil assembly to the tubular body portion.

The support structure may include an aperture formed therein. Accordingly, the method may further include the step of inserting one of the first shaft of the anvil assembly and the second shaft of the tubular body portion into the aperture of the support structure prior to the step of attaching the first shaft of the anvil assembly to the second shaft of the tubular body portion.

The tubular body portion may carry a plurality of surgical staples. The surgical staples may be disposed radially outward of the annular knife. Accordingly, in use, firing the surgical anastomosis device includes deploying the plurality of staples so that the staples penetrate a first interstitial section, the support structure and then a second interstitial section.

The support structure may include a body and a first and a second membrane extending radially outward from the body. Each of the first and second membranes of the support structure may be made from a polymeric film, such as, for example, polyethylene.

In use, expanding the at least one layer of expandable material may include deploying the first and second membranes from a rolled-up condition to an expanded condition. In the expanded condition, the first membrane may extend in a substantially distal direction from the body portion of the support structure and the second membrane may extend in a substantially proximal direction from the body portion of the support structure.

The method may further include the step of pulling on at least one rip-cord to expand the first and second membranes.

Each membrane of the support structure may include a first inner layer and a second outer layer. Accordingly, expanding the at least one layer may include expanding the second outer layer at a greater rate than the first inner layer. The second outer layer of each membrane of the support structure may swell at a rate greater than the first inner layer.

The second outer layers of the first and second membranes may be made from a hydrogel. The first inner layer of each of the first and second membranes of the support structure may be constructed from a substantially non-absorbable material. The first inner layer of each of the first and second membranes may be fabricated from a bio-absorbable mesh fabric. The body may be perforated or porous.

The at least one layer of expandable material may expand upon fluid absorption.

The body may be fabricated from at least one of a polyglactic material, a glycolide homopolymer, and a synthetic absorbable lactomer 9-1 material. The body may be a mesh or other fabric.

The body may include a wound treatment material. The wound treatment material is desirably at least one of an adhesive, a sealant, a hemostat, and a medicament.

The body may be compressible so that the outer terminal edge of the body extends beyond the outer radial surface of the anvil and tubular body portion. Accordingly, the body may be fabricated from foam. The body has a first thickness greater than one quarter of a diameter of the body.

The support structure has an unhydrated condition wherein the body has a first diameter and a first thickness, and a hydrated condition wherein the body has a second diameter greater than the first diameter and a second thickness greater than the first thickness. The body desirably expands from the first diameter and the first thickness to a second diameter and a second thickness upon application of a fluid thereto.

The body may be constructed from a first part of a two-part wound treatment material, and the fluid applied thereto is a second part of the two-part wound treatment material.

According to yet another aspect of the present disclosure, a method of performing a surgical anastomosis procedure is provided. The method includes the steps of providing an anastomosis apparatus having an anvil assembly movably mounted with respect to a tubular body portion; providing a support structure including a body having an outer terminal edge, and an aperture therethrough, the body being compressible; disposing an anvil assembly into a first intestinal section; disposing a distal end portion of the surgical stapling apparatus in a second intestinal section; positioning the support structure on a shaft of the anvil assembly; approximating the anvil assembly and the tubular body portion to capture the body of the support structure between the first intestinal section and the second intestinal section and to compress the body portion therebetween so that the body extends radially beyond the anvil member and the tubular body portion to seal the perimeter of the anastomosis site; and firing the anastomosis apparatus to join the first intestinal section, support structure, and second intestinal section.

The support structure may have an unhydrated condition wherein the body has a first diameter and a first thickness, and a hydrated condition wherein the body has a second diameter greater than the first diameter and a second thickness greater than the first thickness. The support structure may be pre-mounted onto the shaft of the anvil assembly prior to positioning of the anvil assembly in the first intestinal section. Accordingly, prior to approximating the anvil assembly and the tubular body portion, the method further includes the step of hydrating the support structure to expand the body from the first diameter and the first thickness to a second diameter and a second thickness.

The body may be constructed from a first part of a two-part wound treatment material, and the fluid applied thereto is a second part of the two-part wound treatment material.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 13 is a longitudinal cross-sectional view illustrating the anvil rod mounted to the annular stapling device within a surgical site and the support structure of FIGS. 10-12, in an undeployed condition, disposed between the apposed surfaces of the tissue;

FIG. 14 is a longitudinal cross-sectional view illustrating the anvil rod mounted to the annular stapling device within a surgical site and the support structure of FIGS. 10-12, in a deployed condition, disposed between the apposed surfaces of the tissue;

DETAILED DESCRIPTION OF EMBODIMENTS

Figure 1:
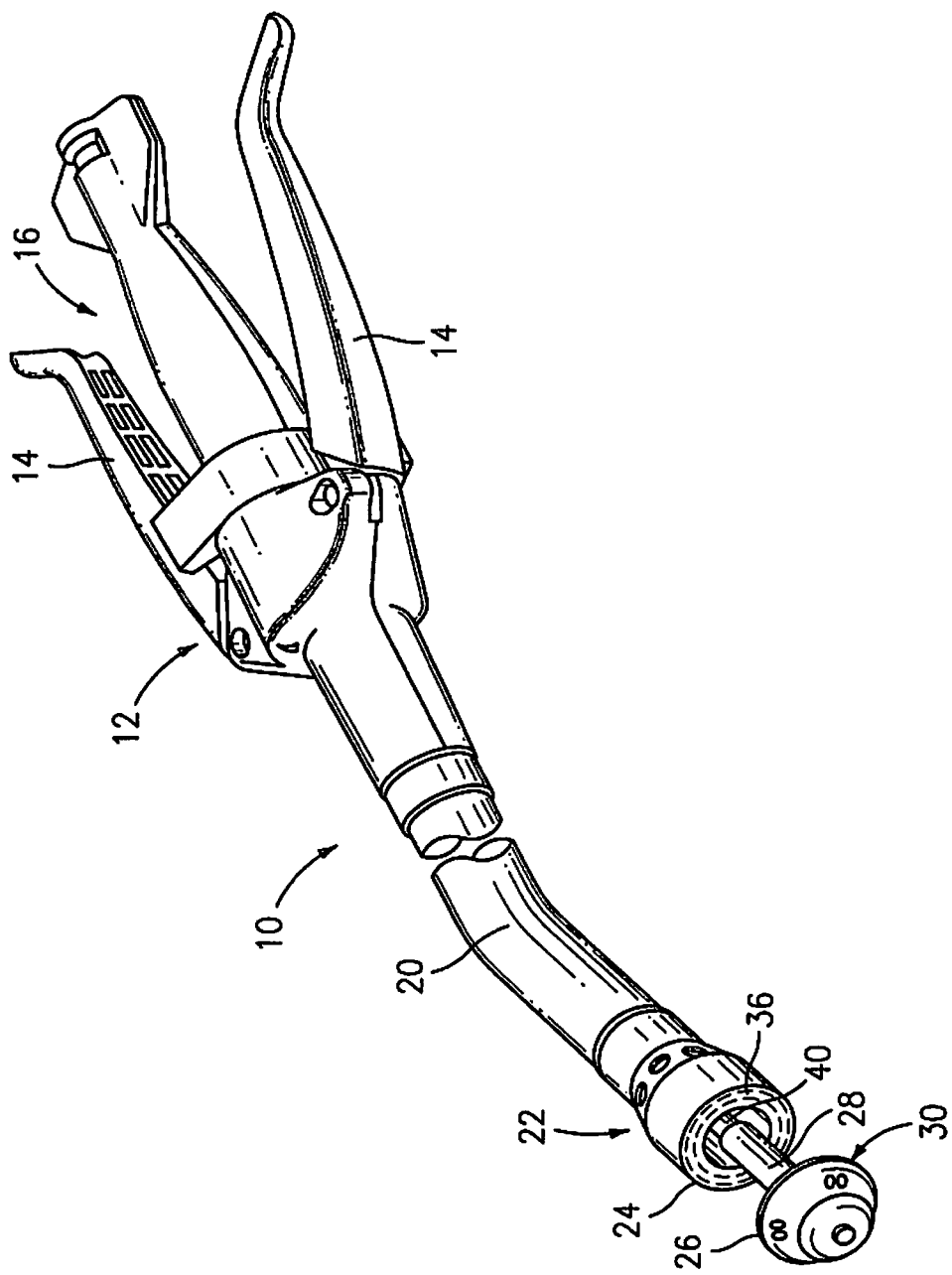
FIG. 1 is a perspective view of an exemplary annular surgical stapling device.

Embodiments of the presently disclosed annular adhesive structures will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Referring initially to FIG. 1, an annular surgical stapling device, for use with the annular adhesive structures disclosed herein, is generally designated as 10. Surgical stapling device 10 includes a handle assembly 12 having at least one pivotable actuating handle member 14, and an advancing member 16. Extending from handle member 12, there is provided a tubular body portion 20 which may be constructed so as to have a curved shape along its length. Body portion 20 terminates in a staple cartridge assembly 22 which includes a pair of annular arrays of staple receiving slots 36 having a staple (not shown) disposed in each one of staple receiving slots 36. Positioned distally of staple cartridge assembly 22 there is provided an anvil assembly 30 including an anvil member 26 and a shaft 28 operatively associated therewith for removably connecting anvil assembly 30 to a distal end portion or connection member 40 of stapling device 10.

Staple cartridge assembly 22 may be fixedly connected to the distal end of tubular body portion 20 or may be configured to concentrically fit within the distal end of tubular body portion 20. Typically, staple cartridge assembly 22 includes a staple pusher (not shown) including a proximal portion having a generally frusto-conical shape and a distal portion defining two concentric rings of peripherally spaced fingers (not shown), each one of which is received within a respective staple receiving slot 36.

Typically, a knife (not shown), substantially in the form of an open cup with the rim thereof defining a knife edge, is disposed within staple cartridge assembly 22 and mounted to a distal surface of a staple pusher (not shown). The knife edge is disposed radially inward of the pair of annular arrays of staples. Accordingly, in use, as the staple pusher is advanced, the knife is also advanced axially outward.

Reference may be made to U.S. Pat. No. 5,915,616 to Viola et al., the entire content of which is incorporated herein by reference, for a detailed discussion of annular stapling device 10.

Turning now to FIGS. 2-9, an annular adhesive or support structure, in accordance with an embodiment of the present disclosure, is generally designated as 100. Structure 100 includes a washer-like or disk-like body 102 including a substantially centrally located aperture 104 formed therethrough. Structure 100 is defined by an outer terminal edge 106, an inner terminal edge 108 defining the size of aperture 104, an upper surface 110, and a bottom surface 112.

In one embodiment, structure 100 is sized such that when structure 100 is operatively associated with stapling device 10, as will be described in greater detail below, outer terminal edge 106 extends radially beyond staple retaining pockets 36 of staple cartridge assembly 22. Additionally, aperture 104 of structure 100 is sized to at least receive shaft 28 of anvil assembly 30 therethrough. In another embodiment, the distance between outer terminal edge 106 and inner terminal edge 108 is substantially equal to a width of a tissue contact surface 24 (see FIG. 1) of staple cartridge assembly 22.

It is contemplated that body 102 of structure 100 may be fabricated from or include a surgical grade, biocompatible, non-absorbable (i.e., permanent) mesh or material desirably impregnated with an adhesive, sealant and/or other medicament. For example, body 102 may be fabricated from "TEFLON", which is a registered trademark owned by DuPont de Nemours & Co. It is further contemplated that body 102 may be fabricated from a biocompatible polymeric foam, felt, polytetrafluoroethylene (PTFE), gelatin, fabric or the like, or any other biocompatible material.

Non-absorbable materials used for body 102 include, and are not limited to, those that are fabricated from such polymers as polyethylene, polypropylene, nylon, polyethylene terephthalate, polytetrafluoroethylene, polyvinylidene fluoride, and the like. Further non-absorbable materials include and are not limited to stainless steel, titanium and the like.

In one embodiment, body 102 of structure 100 may be fabricated from a bio-absorbable material which is desirably impregnated with an adhesive, sealant, and/or other medicament (i.e., wound treatment material). Accordingly, in use, the sealant component of structure 100 functions to retard any bleeding which may occur from the tissue, the adhesive component of structure 100 functions to secure the approximated tissue together, and the bio-absorbability of structure 100 allows for the at least a portion of structure 100 to be absorbed into the body after a predetermined amount of time. For example, structure 100 may remain in place in the body for approximately 2-3 weeks in order for the anastomosis to sufficiently heal prior to structure 100 being absorbed into the body.

Bio-absorbable materials used for body 102 of structure 100 include, and are not limited to, those fabricated from homopolymers, copolymers or blends obtained from one or more monomers selected from the group consisting of glycolide, glycolic acid, lactide, lactic acid, p-dioxanone, α-caprolactone, dioxanone, polyalkylene oxides, and trimethylene carbonate. Other bio-absorbable materials include and are not limited to, for example, Polyglycolic Acid (PGA) and Polylactic Acid (PLA). In one embodiment, body 102 may be fabricated from bio-absorbable felt, PTFE, gelatin or any other bio-absorbable materials. Illustrative examples of bioabsorbable materials include DEXON™ mesh, absorbable felts, such as POLYSORB™, and foams, such as polyurethane.

It is envisioned that body 102 of structure 100 may be impregnated with a wound treatment material "W" which is a pre-cured adhesive or sealant. The pre-cured sealant or adhesive will react with the moisture and/or heat of the body tissue to thereby activate the sealing and/or adhesive properties of the sealant or adhesive. It is envisioned that the pre-cured sealant or adhesive may be a hydro-gel or the like.

It is contemplated that the wound treatment material "W" is any material for joining, healing, sealing or otherwise treating tissue. In a preferred embodiment, the wound treatment material is a bio-compatible sealant, including, and not limited, to sealants which cure upon tissue contact, sealants which cure upon exposure to ultraviolet (UV) light, sealants which are multiple-part systems, including two-part systems which are kept isolated from one another and are combined, or any combinations thereof. Any known suitable adhesive may be used. In one embodiment, it is contemplated that such sealants and/or adhesives are curable. For example, sealants may have a cure time of from about 10 to 15 seconds may be used. In preferred embodiments, the sealant and/or adhesive is a bioabsorbable and/or bio-resorbable material. In another embodiment, it is contemplated that a sealant and/or adhesive having a cure time of about 30 seconds may be used. It is further envisioned that wound treatment material "W" may be a pre-cured adhesive or sealant.

In certain preferred embodiments, the wound treatment material comprises a sealant. Such a sealant is desirably a PEG-based material. Examples of classes of materials useful as the sealant and/or adhesive include acrylate or methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, or water-soluble carbodiimides, anionic polysaccharides in the presence of polyvalent cations, etc.

Some specific materials which may be utilized include isocyanate terminated hydrophilic urethane prepolymers derived from organic polyisocyanates and oxyethylene-based diols or polyols, including those disclosed in U.S. Pat. Nos. 6,702,731 and 6,296,607 and U.S. Published Patent Application No. 2004/0068078; alpha-cyanoacrylate based adhesives including those disclosed in U.S. Pat. No. 6,565,840; alkyl ester based cyanoacrylate adhesives including those disclosed in U.S. Pat. No. 6,620,846; adhesives based on biocompatible cross-linked polymers formed from water soluble precursors having electrophilic and nucleophilic groups capable of reacting and cross-linking in situ, including those disclosed in U.S. Pat. No. 6,566,406; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisocyanate compounds as disclosed in U.S. Published Patent Application No. 2003/0032734, the contents of which are incorporated by reference herein; and isocyanate terminated hydrophilic urethane prepolymers derived from aromatic diisocyanates and polyols as disclosed in U.S. Published Patent Application No. 2004/0115229, the contents of which are incorporated by reference herein.

It is envisioned and within the scope of the present disclosure that wound treatment material "W" may include one or a combination of adhesives, hemostats, sealants, or any other tissue or wound-treating material. Surgical biocompatible wound treatment materials "W", which may be used in accordance with the present disclosure, include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. Hemostats herein include astringents, e.g., aluminum sulfate, and coagulants.

The medicament may include one or more medically and/or surgically useful substances such as drugs, enzymes, growth factors, peptides, proteins, pigments, dyes, diagnostic agents or hemostasis agents, monoclonal antibodies, or any other pharmaceutical used in the prevention of stenosis. The medicament may be disposed on structure 100 or impregnated into structure 100. The medicament may include one or more medically and/or surgically useful substances such as drugs, enzymes, growth factors, peptides, proteins, dyes, diagnostic agents or hemostasis agents, monoclonal antibodies, or any other pharmaceutical used in the prevention of stenosis.

Wound treatment material "W" may include visco-elastic film forming materials, cross-linking reactive agents, and energy curable adhesives. It is envisioned that wound treatment material "W", and in particular, adhesive may be cured with the application of water and/or glycerin thereto. In this manner, the water and/or glycerin cure the adhesive and hydrate the wound.

It is further contemplated that wound treatment material "W" may include, for example, compositions and/or compounds which accelerate or beneficially modify the healing process when particles of the composition and/or compound are applied to or exposed to a surgical repair site. For example, the wound treatment material "W" may be a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, wound treatment material "W" may include one or several growth promoting factors, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

In one embodiment, it is contemplated that body 102 of structure 100 may be impregnated with a first component of a multiple-part adhesive and that the staples, retained in staple receiving slots 36 of staple cartridge assembly 22, may be coated with a second component (e.g., a reactant) of the multiple-part adhesive. In this manner, the first component of the adhesive is activated when the staples penetrate and capture body 102 of structure 100 during the firing sequence of surgical stapling device 10, and the two components of the adhesive contact one another.

As seen in FIGS. 2-9, in an embodiment annular support structure 100 includes at least one, preferably a pair of drapes, skirts or membranes 140, 142 (e.g., a first membrane 140 and a second membrane 142) extending from outer terminal edge 106 of body 102. Desirably, membranes 140, 142 are fabricated from a polymeric or plastic film including and not limited to polyethylene and the like. Each membrane 140, 142 includes a first or outer surface 140a, 142a, respectively, and a second or inner surface 140b, 142b, respectively.

Figure 2:
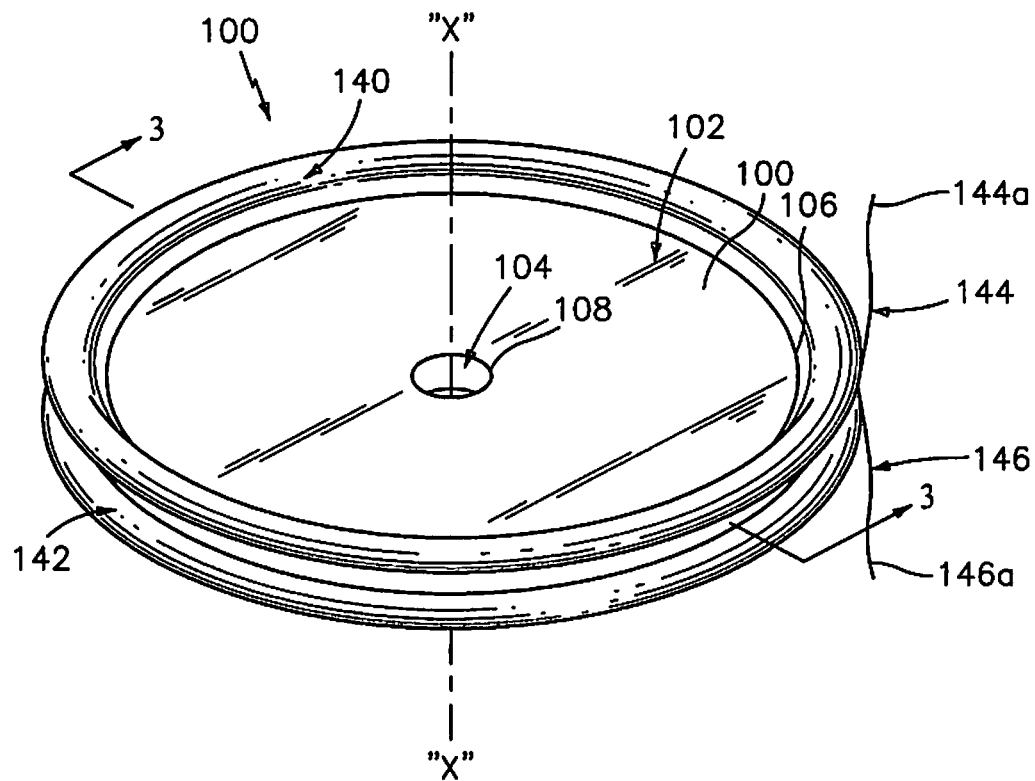
FIG. 2 is a perspective view of a support structure in accordance with an embodiment of the present disclosure, shown in an undeployed condition.
Figure 3:
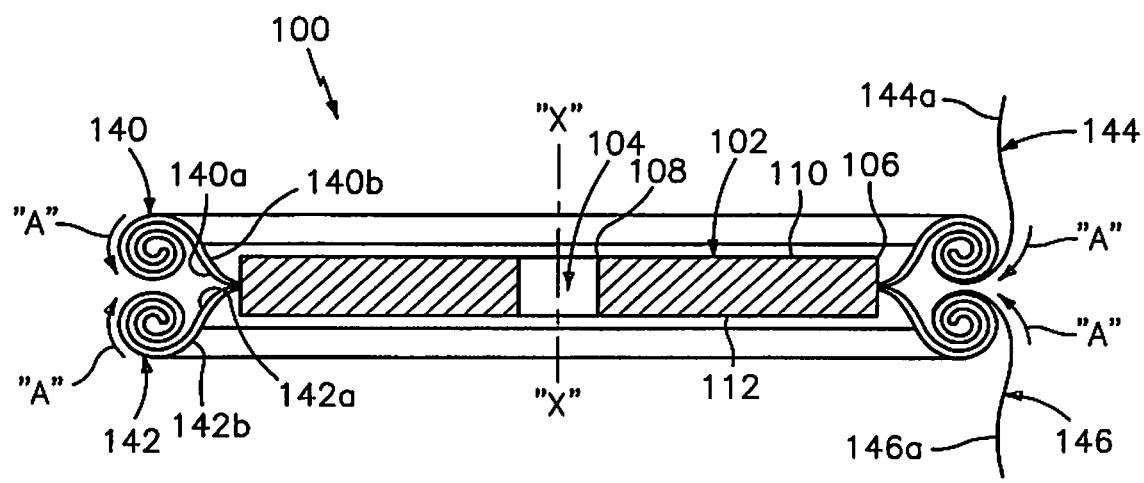
FIG. 3 is a cross-sectional view of the support structure of FIG. 2, as taken through 3-3 of FIG. 2.
Figure 4:
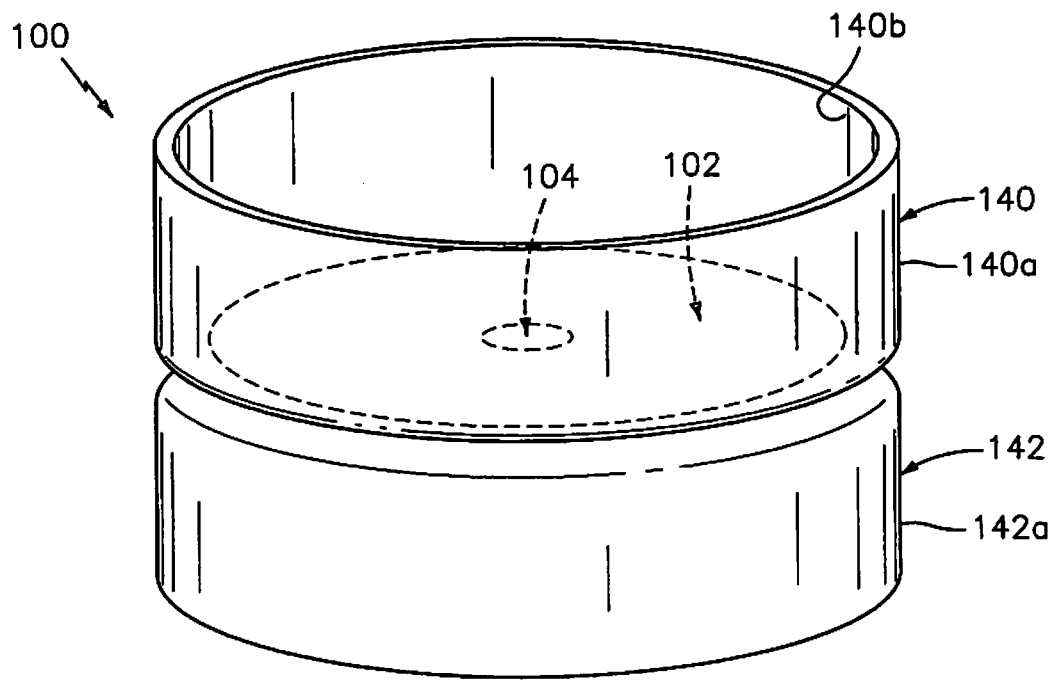
FIG. 4 is a perspective view of the support structure of FIGS. 2 and 3, shown in a deployed condition.
Figure 5:
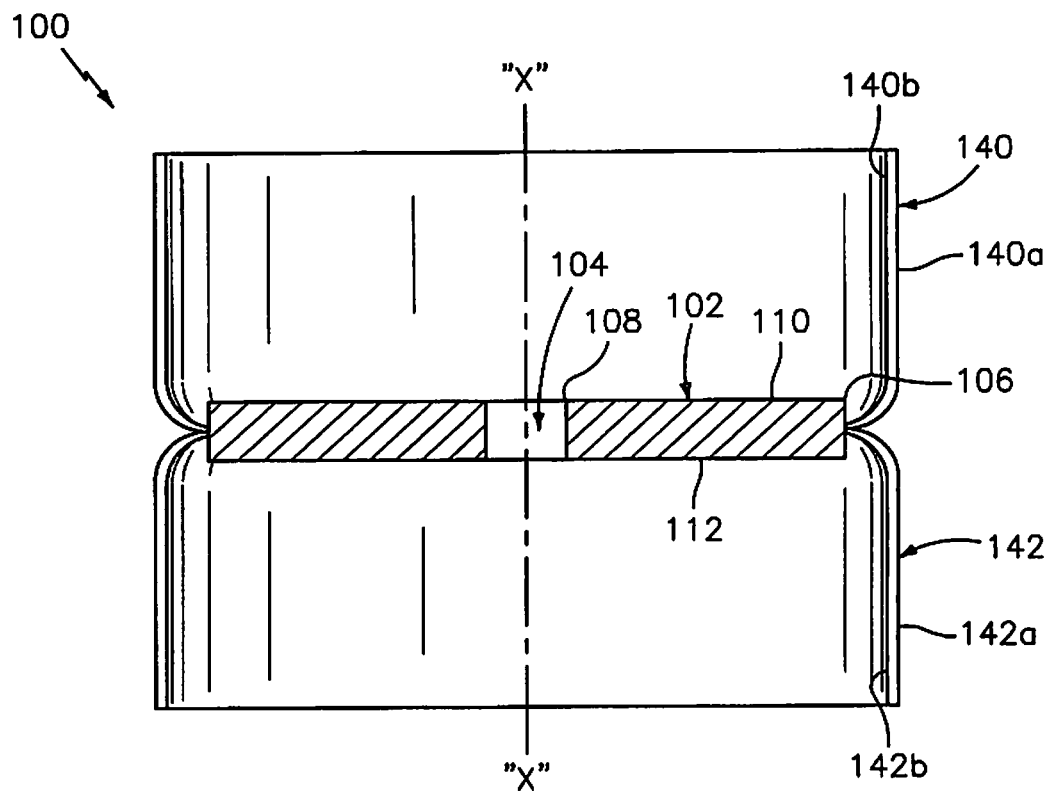
FIG. 5 is a cross-sectional view of the support structure of FIG. 4, shown in the deployed condition.
Figure 6:
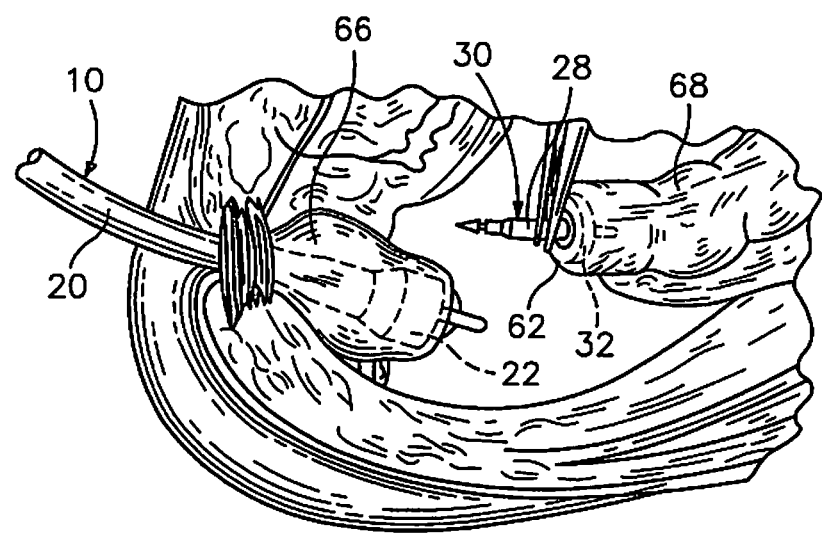
FIG. 6 is a perspective view of the intestinal area of a patient, illustrating a method of positioning the support structure of FIGS. 2-5 on the anvil rod of the annular stapling device of FIG. 1.
Figure 7:
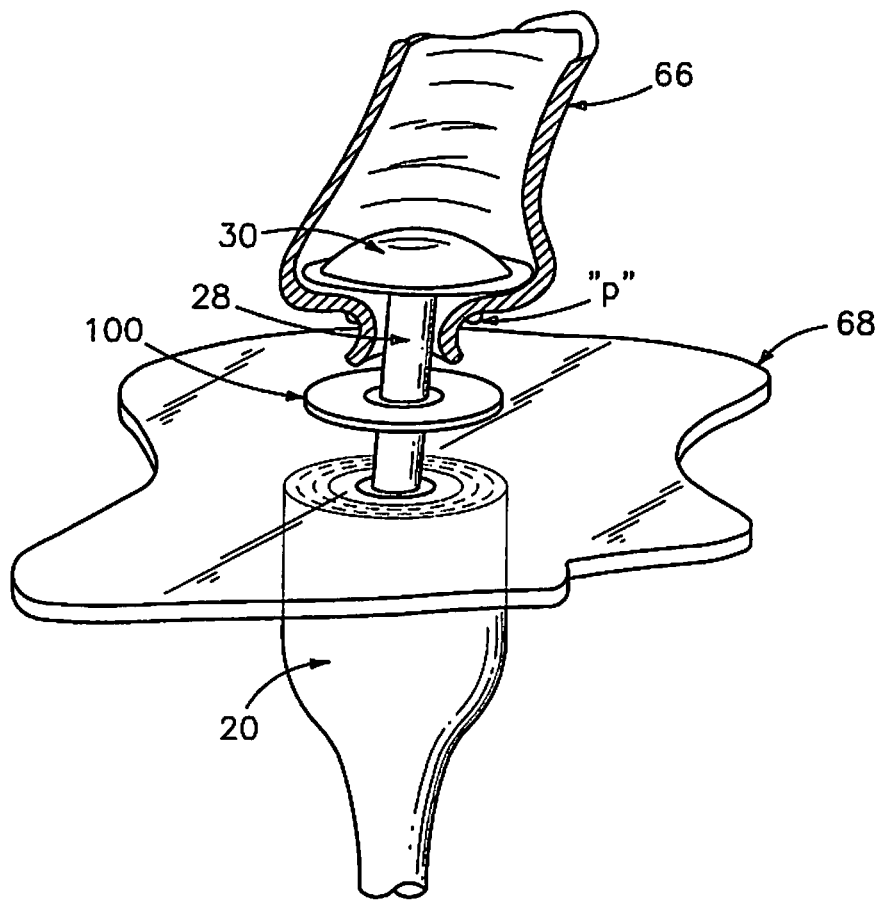
FIG. 7 is a schematic perspective view of the intestinal area of FIG. 6, illustrating the anvil rod mounted to the annular stapling device and having the support structure of FIGS. 2-5 disposed therebetween.

As seen in FIGS. 2 and 3, membranes 140, 142 have a first, undeployed condition wherein membranes 140, 142 are rolled-up towards body 102. Desirably, membranes 140, 142 are rolled under in a direction toward the first or outer surfaces 140a, 142a thereof, as indicated by arrows "A" of FIG. 3. As seen in FIGS. 4 and 5, membranes 140, 142 have a second, deployed condition wherein membranes 140, 142 are unrolled or unfurled to extend in a substantially parallel orientation with respect to the central "X" axis. As will be described in greater detail below, first membrane 140 is unrolled in a first direction, preferably in a distal direction (e.g., in a direction substantially orthogonal to upper surface 110 of body 102), and second membrane 142 is unrolled in a second direction, preferably in a proximal direction (e.g., in a direction substantially orthogonal to lower surface 112 of body 102).

As seen in FIGS. 2 and 3, support structure 100 desirably includes a rip-cord or tether 144, 146 rolled-up into membranes 140, 142. Rip-cords 144, 146 include free ends 144a, 146a which extend from membranes 140, 142 when membranes 140, 142 are in the rolled-up condition. In this manner, as will be described in greater detail below, as rip-cords 144, 146 are pulled, desirably in a distal direction (e.g., orthogonal to upper surface 110 of body 102) and a proximal direction (e.g., orthogonal to lower surface 112 of body 102), membranes 140, 142 are un-rolled or un-furled accordingly.

In one embodiment, it is envisioned that body 102 of support structure 100 is formed of a foam material overmolded onto a relatively thin flexible material or film making up membranes or sleeves 140, 142. Desirably, when un-rolled or un-furled, each membrane 140, 142 extends approximately 2.0 cm from body 102. In other words, when un-rolled or un-furled, first membrane 140 extends from body 102 by approximately 2.0 cm from upper surface 110 of body 102, and second membrane 142 extends from body 102 approximately 2.0 cm from lower surface 112 of body 102.

Turning now to FIGS. 6-9, there is illustrated the use of surgical stapling device 10 and support structure 100 in an anastomosis procedure to effect joining of intestinal sections 66 and 68. The anastomosis procedure is typically performed using minimally invasive surgical techniques including laparoscopic means and instrumentation. At the point in the procedure shown in FIG. 6, a diseased intestinal section has been previously removed, anvil assembly 30 has been introduced to the operative site either through a surgical incision or trans-anally and positioned within intestinal section 68, and tubular body portion 20 of surgical stapling device 10 has been inserted trans-anally into intestinal section 66. Intestinal sections 66 and 68 are also shown temporarily secured about their respective components (e.g., shaft 28 of anvil assembly 30, and the distal end of tubular body portion 20) by conventional means such as a purse string suture "P".

Annular support structure 100 is then placed onto shaft 28 of anvil assembly 30 prior to the coupling of anvil assembly 30 to the distal end of tubular body portion 20. In particular, shaft 28 of anvil assembly 30 is inserted into aperture 104 of body portion 102. Following positioning of structure 100 onto shaft 28 of anvil assembly 30, the surgeon maneuvers anvil assembly 30 until the proximal end of shaft 28 is inserted into the distal end of tubular body portion 20 of surgical stapling device 10, wherein the mounting structure (not shown) within the distal end of tubular body portion 20 engages shaft 28 to effect the mounting.

Figure 8:
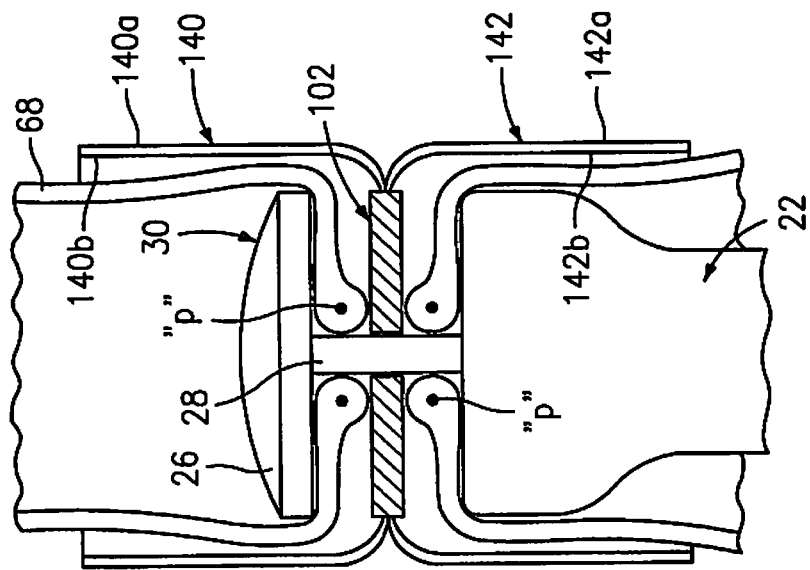
FIG. 8 is a longitudinal cross-sectional view illustrating the anvil rod mounted to the annular stapling device within a surgical site and the support structure of FIGS. 2-5, in an undeployed condition, disposed between the apposed surfaces of the tissue.
Figure 9:
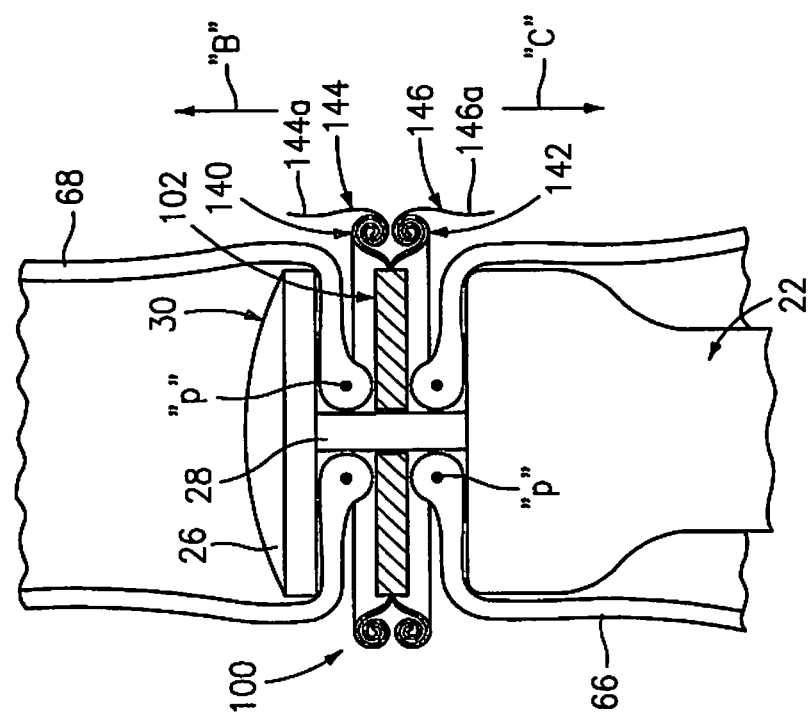
FIG. 9 is a longitudinal cross-sectional view illustrating the anvil rod mounted to the annular stapling device within a surgical site and the support structure of FIGS. 2-5, in a deployed condition, disposed between the apposed surfaces of the tissue.
Figure 10:
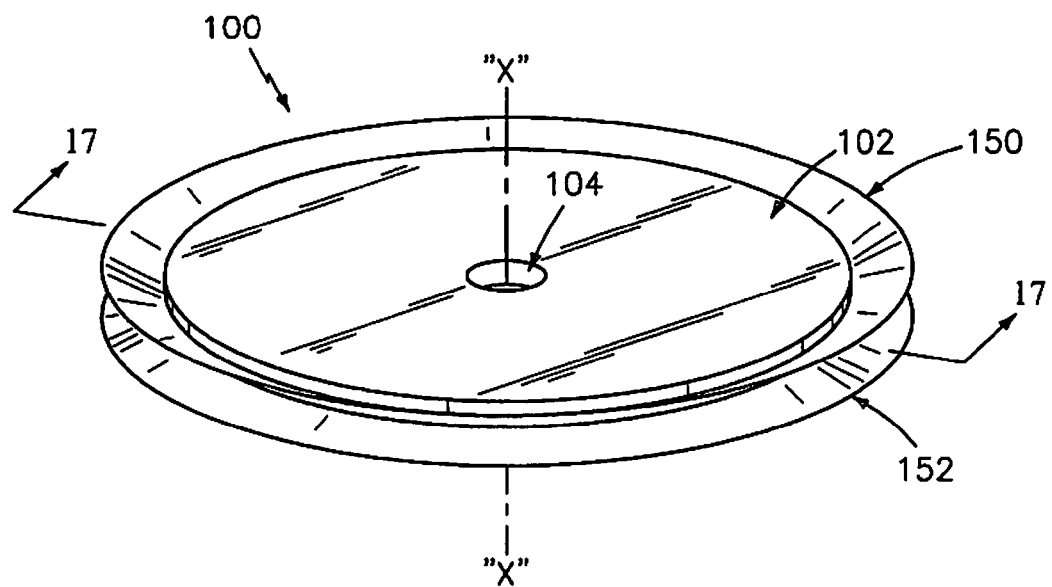
FIG. 10 is a perspective view of an support structure according to an alternate embodiment of the present disclosure.
Figure 11:
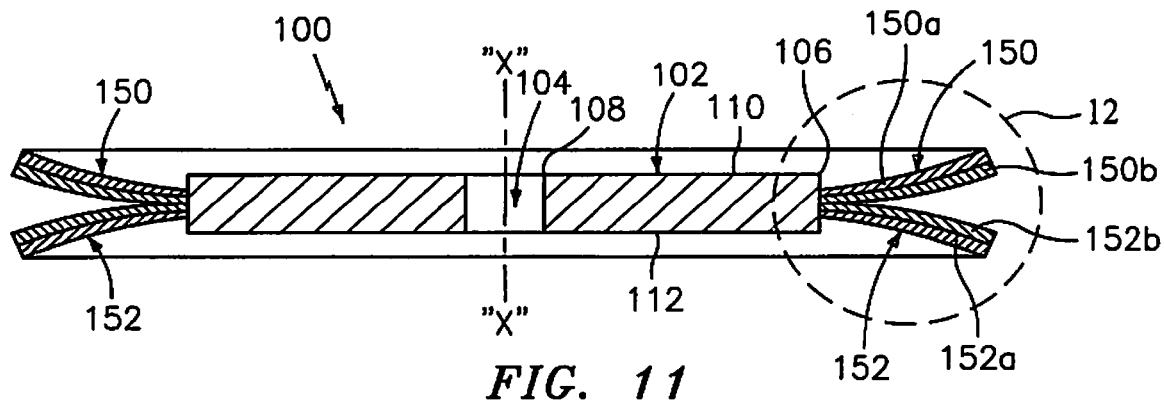
FIG. 11 is a cross-sectional view of the support structure of FIG. 10, as taken through 11-11 of FIG. 10.

Thereafter, as seen in FIG. 8, anvil assembly 30 and tubular body portion 20 are approximated to approximate intestinal sections 66, 68 and capture body 102 of annular support structure 100 therebetween. With body 102 captured between intestinal sections 66, 68, as seen in FIG. 9, membranes 140, 142 are deployed (i.e., un-rolled or un-furled) as described above. In particular, first membrane 140 is un-rolled or un-furled in a distal direction, as indicated by arrow "B", so as to over-lie intestinal section 68, and second membrane 142 is un-rolled or un-furled in a proximal direction, as indicated by arrow "C", so as to over-lie intestinal section 66. Desirably, first and second membranes 140, 142 are un-rolled or un-furled by pulling on rip-cords 144, 146 in a distal or proximal direction, as necessary.

Figure 15:
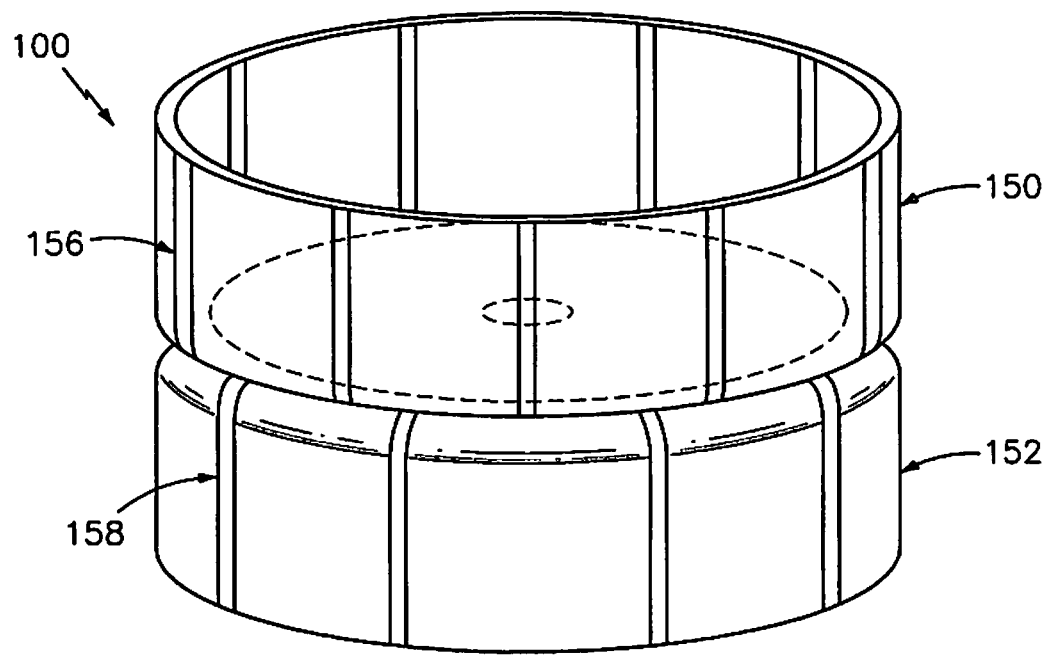
FIG. 15 is a perspective view of a support structure according to yet another alternate embodiment of the present disclosure.
Figure 16:
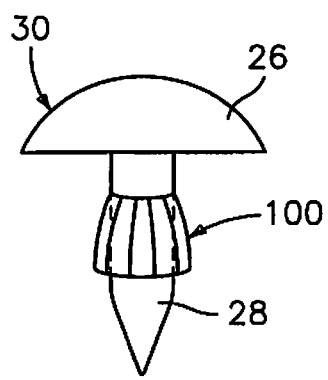
FIG. 16 is a schematic perspective view of an anvil assembly of the annular stapling device of FIG. 1 including yet another support structure operatively associated therewith and in an unexpanded condition.
Figure 17:
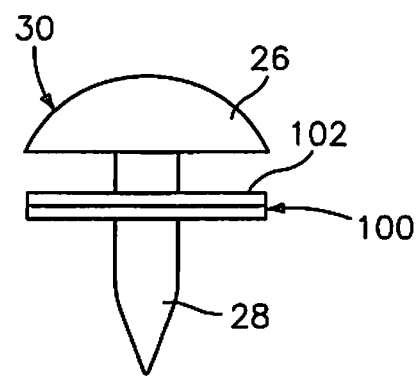
FIG. 17 is a schematic side elevational view of the anvil assembly of FIG. 16 illustrating the support structure in an expanded condition.

Membranes 140, 142 extend a predetermined distance over intestinal sections 66 and 68 (e.g., approximately 2 cm). When un-rolled or un-furled, membranes 140, 142 will adhere to the surface of intestinal sections 66, 68. Membranes 140 and 142 function to inhibit leakage from the anastomosis site and/or function to strengthen or reinforce intestinal sections 66, 68. With membranes 140, 142 deployed, as seen in FIG. 15, surgical stapling device 10 may be fired thereby stapling intestinal sections 66, 68 to one another and cutting the portion of tissue and structure 100 disposed radially inward of the knife, to complete the anastomosis.

Turning now to FIGS. 10-14, annular support structure 100 includes at least one, preferably a pair of membranes 150, 152 (e.g., a first membrane 150 and a second membrane 152) extending from outer edge 106 of body 102. Each membrane 150 and 152 includes two layers, an inner layer 150a, 152a, respectively, and an outer layer 150b, 152b, respectively. Desirably, the materials selected for the construction of membranes 150, 152 swell at different rates when in the presence of moisture or fluid. In this manner, membranes 150, 152 will tend to bend or curl about the layer having the relatively slower rate of fluid swelling or fluid absorption. In this manner, support structure 100 has a first undeployed condition in which membranes 150, 152 extend substantially radially outward from body 102, and a second deployed condition in which membranes 150, 152 are substantially aligned with the central "X" axis of body 102.

In accordance with one embodiment, it is envisioned that inner layer 150a, 152a of membranes 150, 152 are constructed from a substantially non-absorbable (i.e., does not absorb moisture therein) or non-expanding (i.e., static) material, such as, for example, a bio-absorbable or resorbable mesh fabricated from polyglycolic acid, sold under the tradename DEXON™, available from Tyco Healthcare Group LP, Norwalk, Conn. Other mesh, knit, woven and non-woven materials may be used. It is also envisioned that outer layer 150b, 152b of membranes 150, 152 are constructed from an absorbable, resorbable or expanding (i.e., dynamic) material, such as, for example, hydrogel and the like.

Desirably, each membrane 150 and 152 includes a hydrogel outer layer 150b, 152b laminated to a bio-absorbable mesh inner layer 150a, 152a. Furthermore, support structure 100 includes a foam body 102 laminated over a pair of dual layered membranes 150, 152. While each membrane 150, 152 desirably includes a pair of layers, it is envisioned and within the scope of the present disclosure for membranes 150, 152 to include any number of layers.

Figure 12:
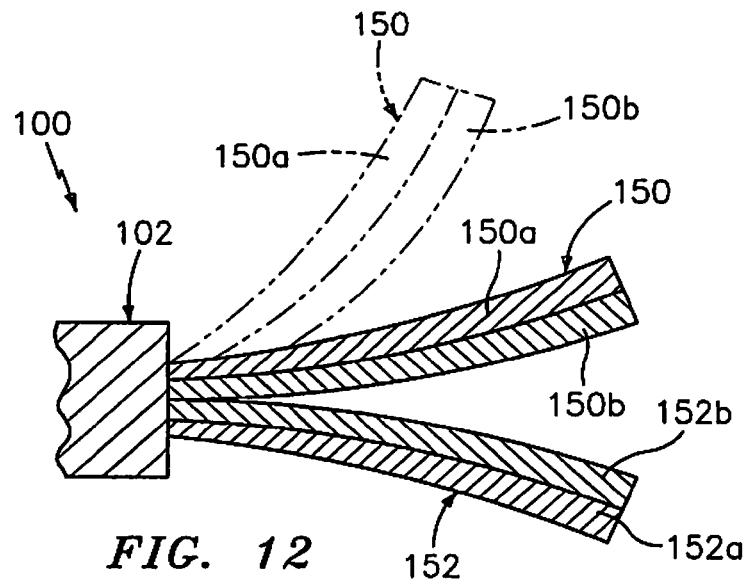
FIG. 12 is an enlarged view of the indicated area of detail of FIG. 11.

Accordingly, with reference to FIG. 12, the difference in material properties between inner layers 150a, 152a and outer layers 150b, 152b of membranes 150, 152 cause membranes 150, 152 to curl or bend from the undeployed condition, wherein membranes 150, 152 extend in a substantially radial direction, to a deployed condition, wherein membranes 150, 152 extend in a direction substantially parallel to the central "X" axis (as shown in phantom in FIG. 12).

Turning now to FIGS. 13 and 14, there is illustrated the use of surgical stapling device 10 and support structure 100 including membranes 150, 152 in an anastomosis procedure to effect joining of intestinal sections 66 and 68. At the point in the procedure shown in FIG. 13, anvil assembly 30 and tubular body portion 20 are shown approximated to one another to capture body 102 of annular support structure 100 between intestinal sections 66 and 68, wherein intestinal section 66 and 68 were previously secured about their respective components (e.g., shaft 28 of anvil assembly 30, and the distal end of tubular body portion 20) by conventional means such as a purse string suture "P", annular support structure 100 was positioned between intestinal sections 66 and 68, and anvil assembly 30 was coupled to the distal end of tubular body portion 20.

With body portion 102 of support structure 100 captured between intestinal sections 66, 68, as seen in FIGS. 13 and 14, membranes 150, 152 begin to deploy (i.e., curl or bend from the substantially radially extended orientation to the orientation substantially parallel with the central "X" axis) as described above. In particular, as outer layers 150b, 152b of first and second membranes 150, 152 absorb fluid and swell (i.e., expand), first and second membranes 150, 152 curl or bend to the side of membrane 150, 152 which swells or expands at a rate slower, i.e., toward inner layers 150a, 152a. As membranes 150, 152 are deployed, as indicated by arrow "B", first membrane 150 over-lies intestinal section 68, and second membrane 152 over-lies intestinal section 66, as indicated by arrow "C".

Desirably, membranes 150, 152 extend a predetermined distance over intestinal sections 66 and 68 (e.g., approximately 2 cm). Accordingly, when deployed, membranes 150, 152 will adhere to the surface of intestinal sections 66, 68. Membranes 150, 152 function to inhibit leakage from the anastomosis site and/or function to strengthen or reinforce intestinal sections 66, 68. With membranes 150, 152 deployed, as seen in FIG. 14, surgical stapling device 10 may be fired thereby stapling intestinal sections 66, 68 to one another and cutting the portion of tissue and structure 100 disposed radially inward of the knife, to complete the anastomosis.

As seen in FIG. 15, annular support structure 100 includes a series of ribs 156, 158 provided on and/or in each membrane 150, 152, respectively. Desirably, ribs 156, 158 extend radially around the perimeter or circumference of membranes 150, 152. Ribs 156, 158 are substantially radially oriented.

Ribs 156, 158 are fabricated from a shape memory material, alloy or the like, preferably, NITINOL™ and the like. It is further envisioned that ribs 156, 158 may be fabricated from a bio-absorbable material.

Ribs 156, 158 have a memorized shape which is oriented substantially parallel to the central "X" axis of support structure 100. In this manner, support structure 100 has a first or un-deployed condition in which ribs 156, 158 are in a biased rolled-up condition and membranes 150, 152 are also rolled-up, and a second or deployed condition in which ribs 156, 158 are in their memorized shape or condition and membranes 150, 152 are extended.

In use, with support structure in an un-deployed condition, support structure 100 is positioned in shaft 28 of anvil assembly 30. With support structure 100 so positioned, support structure 100 is deployed when ribs 156, 158 return to their memorized conditions. In particular, the return of ribs 156, 158 to their memorized conditions extends membranes 150, 152 over intestinal sections 66 and 68 and/or in a direction substantially parallel to the central "X" axis.

Turning now to FIGS. 18-28, a support structure in accordance with an alternate embodiment is generally designated as 200. Support structure 200 is substantially similar to support structure 100 and will only be described in detail to the extent necessary to identify differences in construction and operation.

Figure 18:
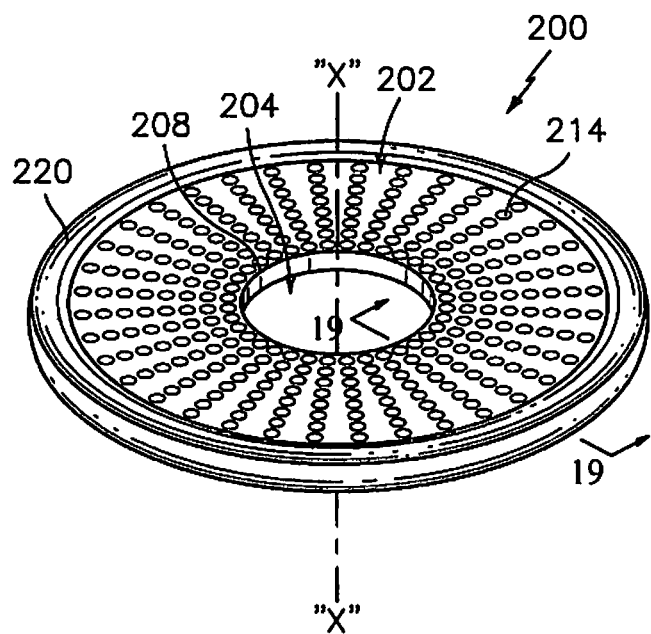
FIG. 18 is a perspective view of a support structure in accordance with another embodiment of the present disclosure, for use with the annular surgical stapling device of FIG. 1.
Figure 19:
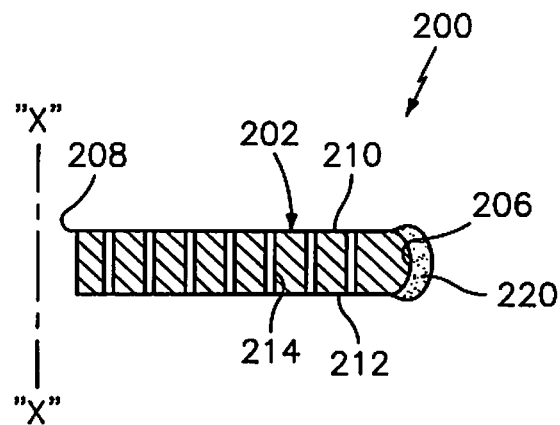
FIG. 19 is a cross-sectional view of the support structure of FIG. 18, as taken through 19-19 of FIG. 18.
Figure 20:
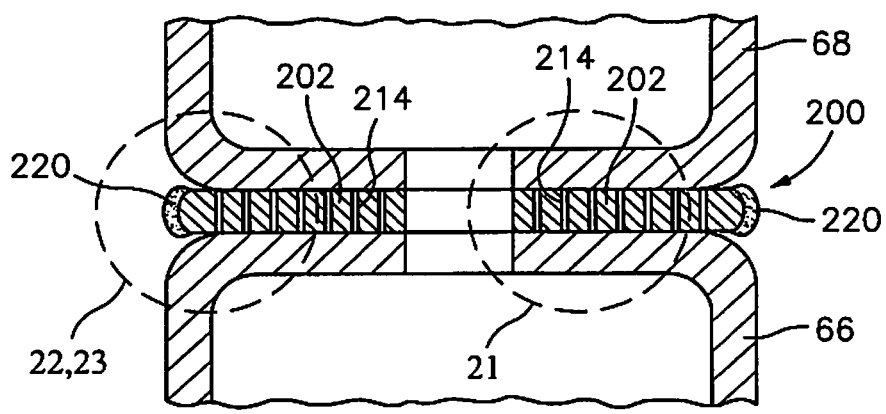
FIG. 20 is a longitudinal cross-sectional view of the intestinal area of the patient following placement of the support structure of FIGS. 18 and 19 and firing of the surgical stapling apparatus.

As seen in FIGS. 18 and 19, body 202 of support structure 200 includes a plurality of pores 214 extending therethrough. Desirably, pores 214 are substantially parallel with the longitudinal "X" axis of body 202. Pores 214 allow for healing to take place between a pair of apposed tissue surfaces. Additionally, since pores 214 are substantially parallel to the longitudinal "X" axis, leakage of fluid from the anastomotic site is reduced. While body 202 has been shown and described as including pores 214, it is envisioned and within the scope of the present disclosure that body 202 may be perforated or may be constructed from a porous material.

With continued reference to FIGS. 18 and 19, support structure 200 includes a rim or layer 220 of fluid expanding or water-swellable material, e.g., a hydrogel, disposed around outer terminal edge 206 of body 202. Hydrogels contemplated for support structure 200 are identified in U.S. Pat. No. 5,505,952 to Jiang et al., the entire content of which is incorporated herein by reference.

Turning now to FIGS. 20-23, there is illustrated the use of support structure 200 in an anastomosis procedure to effect joining of intestinal sections 66 and 68. The anastomosis procedure is typically performed using minimally invasive surgical techniques including laparoscopic means and instrumentation. At the point in the procedure shown in FIG. 20, support structure 200 has been placed onto shaft 28 of anvil assembly 30, the anvil assembly 30 has been coupled to the distal end of tubular body portion 20 of surgical stapling device 10, and surgical stapling device 10 has been fired thereby stapling intestinal sections 66, 68 to one another and cutting the portion of tissue and support structure 200 disposed radially inward of the knife, to complete the anastomosis.

Figure 21:
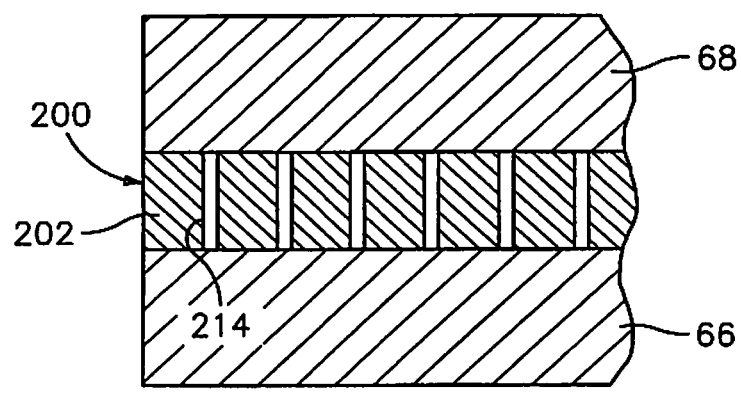
FIG. 21 is an enlarged cross-sectional view, of the indicated area of detail of FIG. 20.

As seen in FIG. 21, pores 214 of body 202 allow for in-growth of intestinal sections 66, 68 therein thereby improving the healing process. In particular, pores 214 of body 202 reduce the time required for intestinal sections 66, 68 to contact one another during the healing process. For example, depending on the size of pores 214 of body 202, intestinal sections 66, 68 may contact one another immediately following the firing of surgical stapling device 10, or pores 214 of body 202 define channels into which intestinal sections 66, 68 may grow and come into contact with one another over time.

Figure 23:
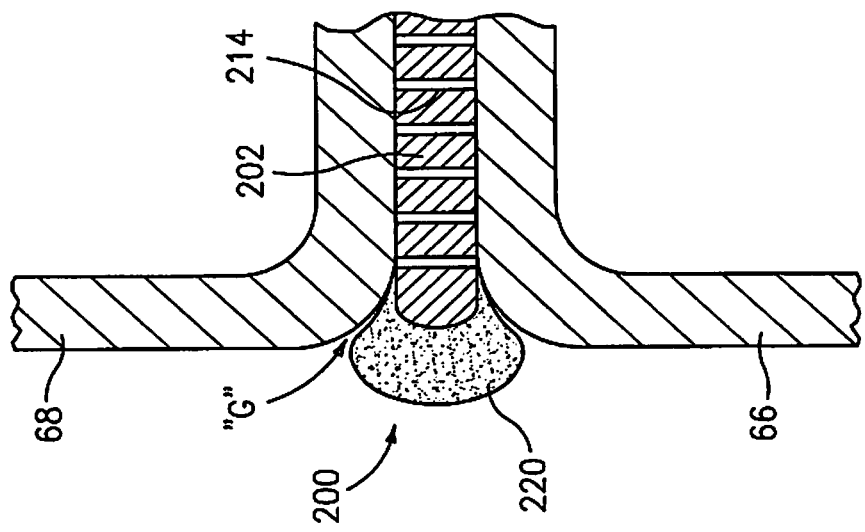
FIG. 23 is an enlarged cross-sectional view, of the indicated area of detail of FIG. 20, illustrating the annular support structure in a second condition.
Figure 22:
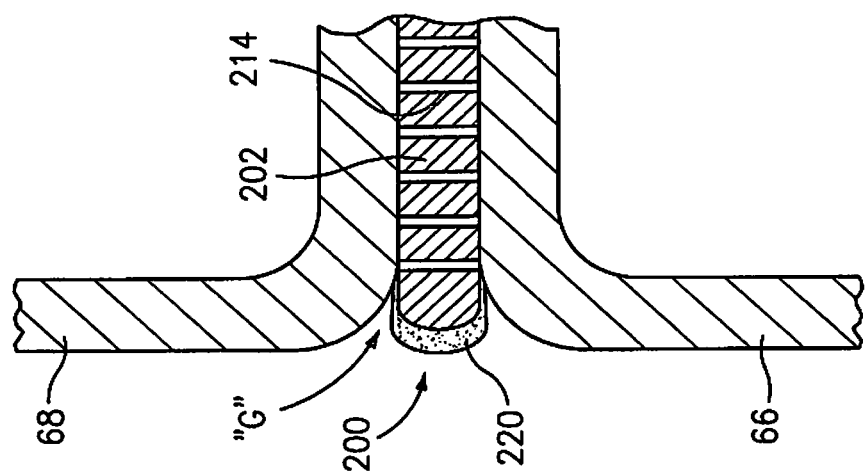
FIG. 22 is an enlarged cross-sectional view, of the indicated area of detail of FIG. 20, illustrating the annular support structure in a first condition.

As seen in FIG. 22, initially, following placement of support structure 200 into position between intestinal sections 66, 68 and firing of surgical stapling device 10, rim 220 of support structure 200 is in a first or unexpanded (i.e., unswelled) condition. Subsequently, as seen in FIG. 23, with support structure 200 in position between intestinal sections 66, 68, rim 220 thereof begins to absorb moisture from the surrounding environment (e.g., water, saline, blood, etc.) and expand to a second or swelled condition. In one method, it is envisioned that fluid may be dispensed onto the anastomosis site, especially onto rim 220 of support structure 200 in order to cause expanding and/or swelling of rim 220.

As seen in FIG. 23, as rim 220 of support structure 200 swells or expands, the radial gap "G" between intestinal sections 66, 68 fills. Accordingly, rim 220, when in the swelled or expanded condition acts as a seal, darn, stopper, barrier or the like to inhibit and/or prevent the leakage of the contents of the bowel into the abdominal region of the patient. In other words, the swelling of rim 220 results in the formation of a gasket-like seal around the outside of the anastomosis.

Figure 24:
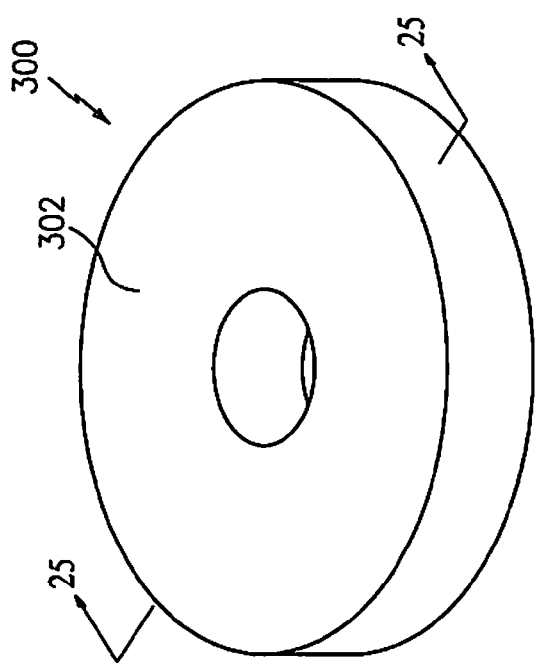
FIG. 24 is a perspective view of a support structure according to an alternate embodiment of the present disclosure.
Figure 25:
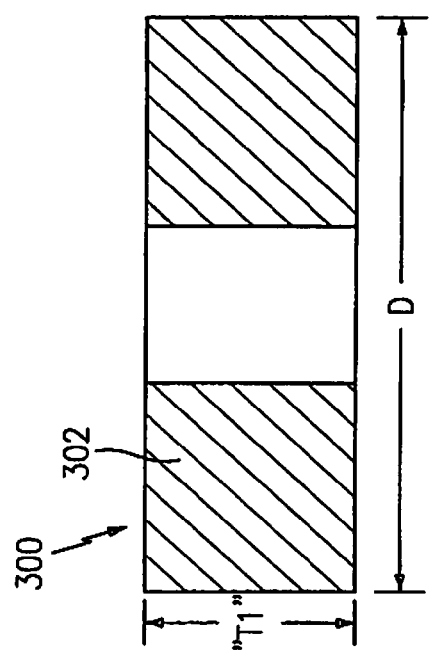
FIG. 25 is a transverse cross-sectional view of the support structure of FIG. 24, as taken through 25-25 of FIG. 10.

Turning now to FIGS. 24-28, a support structure, in accordance with an alternate embodiment of the present disclosure, is generally designated as 300. As seen in FIGS. 24 and 25, body 302 of support structure 300 may be formed entirely of resilient compressible foam or sponge-like material fabricated from a bio-absorbable material or any other bio-compatible material disclosed above with regard to support structure 100. Desirably, as seen in FIG. 25, body 302 of support structure 300 has an initial height or thickness "T1" (e.g., the height or thickness when body 302 is fully expanded). Desirably, body 302 has a diameter "D" which is at least equal to a diameter of tubular body portion 20 and/or anvil member 26. Most desirably, the diameter "D" of body portion of support structure 300 is greater than the diameters of tubular body 20 and/or anvil member 26. Desirably, thickness "T1" is greater than a quarter of the diameter "D", when in the initial uncompressed condition.

Figure 26:
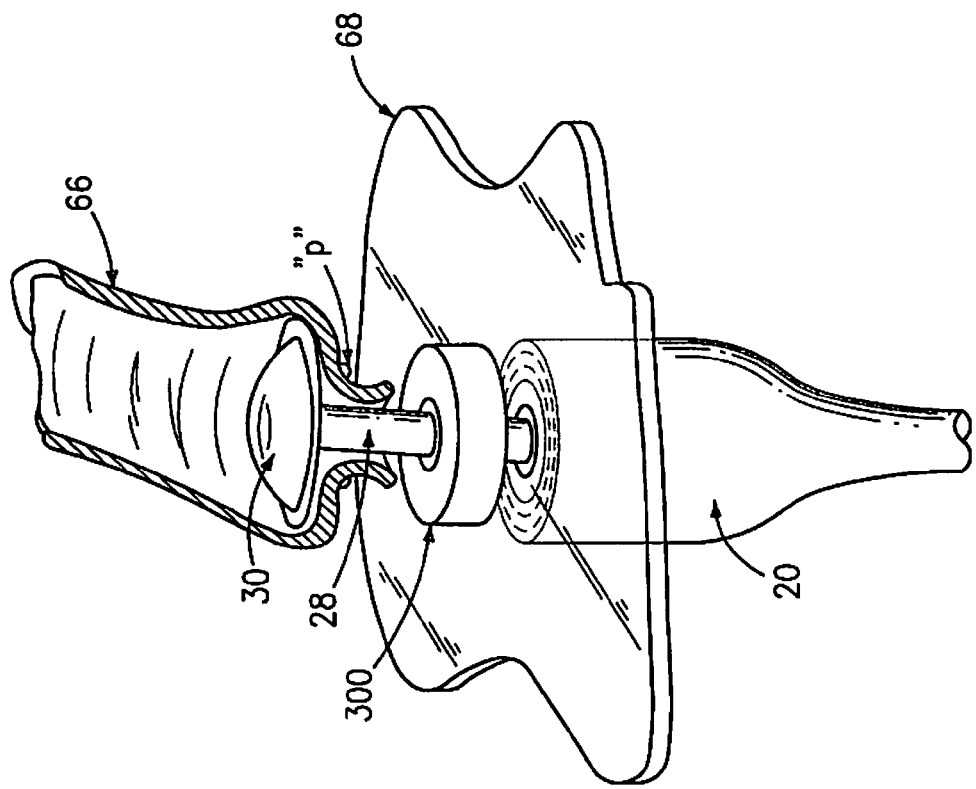
FIG. 26 is a perspective view of the intestinal area of the patient, illustrating the positioning of the support structure of FIGS. 24 and 25 between the anvil assembly and the tubular body portion.
Figure 27:
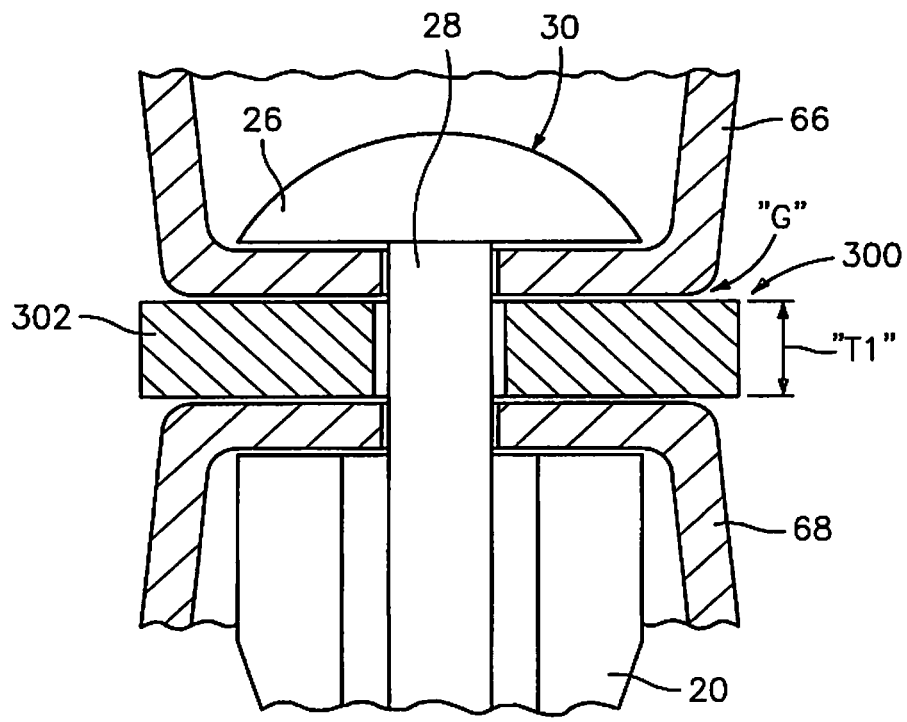
FIG. 27 is a longitudinal cross-sectional view of the intestinal area of the patient illustrating the intestinal sections approximated toward one another to contact the support structure of FIGS. 24 and 25.
Figure 28:
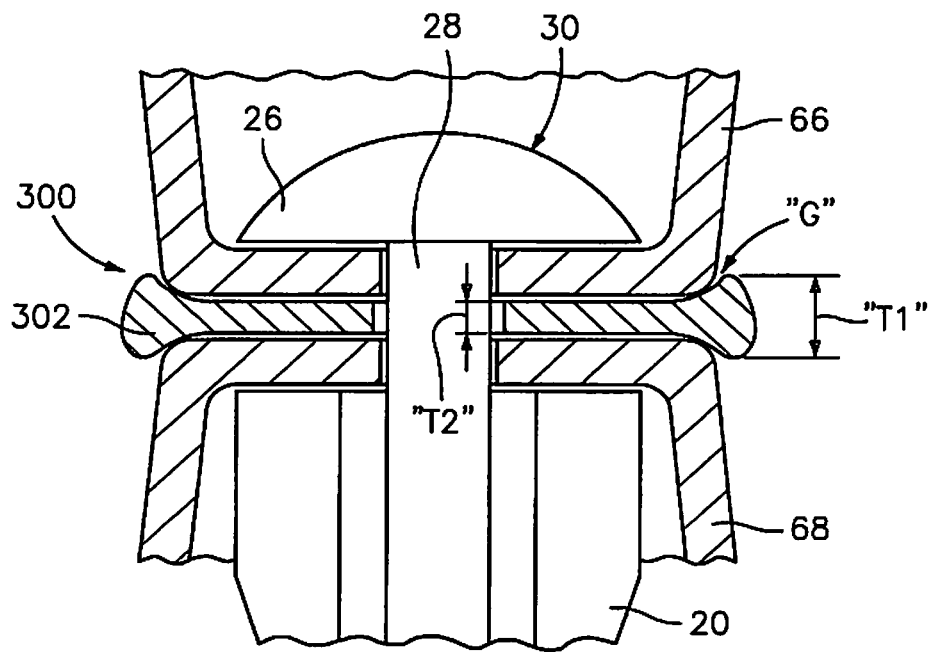
FIG. 28 is a longitudinal cross-sectional view of the intestinal area of the patient illustrating the intestinal sections approximated toward one another to compress the support structure of FIGS. 24 and 25 between the intestinal sections.

Turning now to FIGS. 26-28, there is illustrated the use of surgical stapling device 10 and support structure 300 in an anastomosis procedure to effect joining of intestinal sections 66 and 68. As seen in FIGS. 27 and 28, with a support structure 300 positioned on shaft 28 of anvil assembly 30 and disposed between intestinal sections 66, 68, as anvil assembly 30 and tubular body portion 20 are approximated, body 302 of support structure 300 is compressed therebetween. In particular, as seen in FIG. 27, prior to complete approximation, body 302 of support structure 300 is uncompressed and desirably extends radially beyond the outer terminal edges of tubular body portion 20 and/or anvil member 26. In particular, body 302 of support structure 300 has a thickness substantially equal to "T1". Thereafter, upon complete approximation, body 302 of support structure 300, in the region disposed between tubular body portion 20 and anvil member 26, is compressed therebetween to a thickness "T2". Accordingly, the portion of support structure 300 disposed radially outward of tubular body portion 20 and anvil member 26 remains substantially uncompressed (e.g., having a thickness approximately equal to "T1") thereby filling and/or sealing the radial gap "G" between intestinal sections 66, 68.

In addition to reducing leakage from the anastomosis site, due to the compressible nature of body 302 of support 300, the body 302 is capable of filling any voids or recesses which may exist in the surface of intestinal sections 66, 68.

Following the approximation of anvil assembly 30 and tubular body portion 20, to approximate intestinal sections 66, 68 and capture body 302 of support structure 300 therebetween, surgical stapling device 10 is fired thereby stapling intestinal sections 66, 68 to one another and cutting the portion of tissue and support structure 300 disposed radially inward of the knife, to complete the anastomosis.

Figure 29:
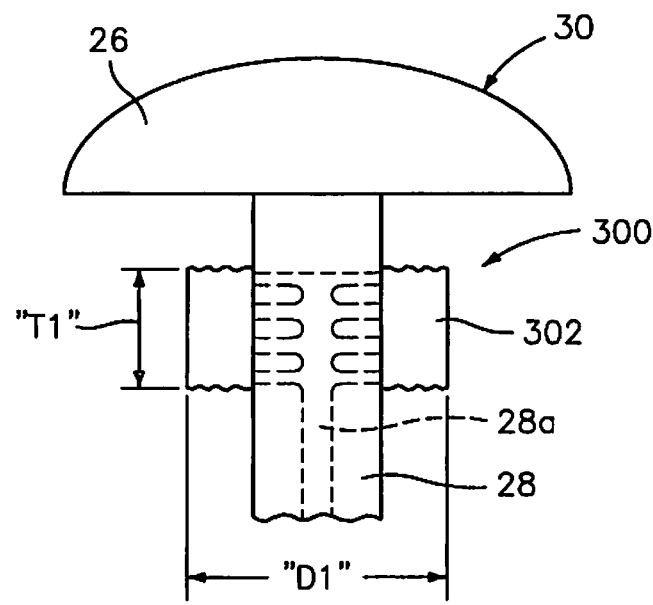
FIG. 29 is a side elevational view of an anvil assembly including the support structure of FIGS. 24 and 25, in an unexpanded condition, operatively secured to the stem thereof.
Figure 30:
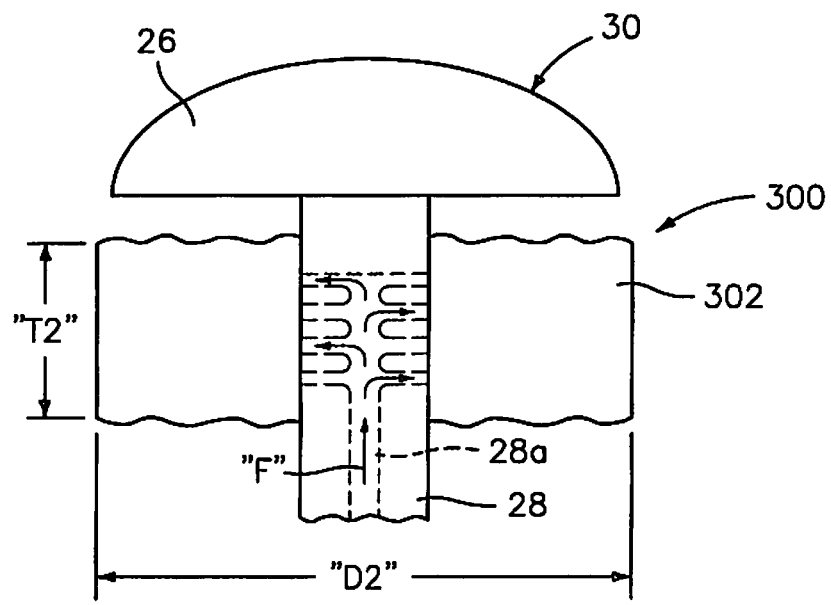
FIG. 30 is a side elevational view of an anvil assembly including the support structure of FIGS. 24 and 25, in an expanded condition, operatively secured to the stem thereof

As seen in FIG. 29, support structure 300 may have an unexpanded (e.g., collapsed or un-hydrated condition) in which body 302 of support structure 300 has a first diameter "D1" and a first thickness "T1". Additionally, as seen in FIGS. 29 and 30, anvil assembly 30 includes a network of channels 28a formed in shaft 28 which are configured and arranged to dispense fluid onto and/or direct fluid into body 302 of support structure 300. While channels 28a have been shown and described, any structure for delivering fluid to body 302 of support structure 300 is contemplated by the present disclosure.

As seen in FIG. 30, fluid "F" is delivered to body 302 of support structure 300 thereby causing body 302 of support structure 300 to expand radially and longitudinally. In other words, the application of fluid "F" to body 302 of support structure 300 causes body 302 of support structure 300 to expand and hydrate. In the expanded condition, body 302 of support structure 300 has a second diameter "D2", larger than first diameter "D1", and a second thickness "T2", larger than first thickness "T1".

In use, with support structure 300 in the un-expanded condition, anvil assembly 30 is introduced into the surgical site as described above. Following connection of anvil assembly 30 to the distal end of tubular body portion 20, fluid "F" is delivered to body 302 of support structure 300, thereby causing support structure 300 to expand. Following expansion of support structure 300, the surgical procedure is continued as described above.

It is envisioned and within the scope of the present disclosure that the fluid "F" may be a cross-linker or other substance which is reactive with the foam of body 302 of support structure 300 to thereby form or create a support structure 300 of wound treatment material (e.g., adhesive, sealant, hemostat, medicament, etc.). It is contemplated that body 302 of support structure 300 may be a foam made from a first part of a multiple-part wound treatment material, and fluid "F" may include a second part of the multiple-part wound treatment material. In this manner, the wound treatment material is formed upon interaction of fluid "F" with body 302 of support structure 300.

From the foregoing, it will be appreciated that the support structures of the present disclosure function to strengthen the anastomosis and reduce the occurrence of bleeding, leaking and stricture. It is also to be appreciated that the support structures of the present disclosure may be utilized in a number of other applications and is not limited solely to bowel or bronchus anastomosis.

While several particular fowls of the support structures have been illustrated and described, it will also be apparent that various modifications can be made without departing from the spirit and scope of the present disclosure. For example, it is envisioned and within the scope of the present disclosure for an ultraviolet light activated adhesive to be used in connection with any of the support structures described above. In use, either prior to or following firing of surgical stapling device 10, the support structure is irradiated with UV light to thereby activate the adhesive thereof.

It is further contemplated that each of the support structures described herein may be used with an annular surgical anastomosing device, not including any staples for securing tissue together, which is capable of approximating, adhering and cutting tissue.

Thus, it should be understood that various changes in form, detail and application of the support structures of the present disclosure may be made without departing from the spirit and scope of the present disclosure.

What is claimed is:

1. A method of disposing a support structure between adjacent intestinal sections, comprising the steps of:
    providing a circular surgical anastomosis device, the circular surgical anastomosis device including:
        an anvil assembly having an anvil member and a first shaft; and
        a tubular body portion having an annular knife operatively disposed therein and a second shaft disposed radially inward of the annular knife, the first shaft of the anvil assembly being selectively attachable to the second shaft of the tubular body;
    inserting the anvil assembly into a first intestinal section;
    inserting the tubular body portion into a second intestinal section;
    disposing a support structure between the first intestinal section and the second intestinal section, the support structure having a body having an outer terminal edge and at least one layer of expandable material extending radially outward from the outer terminal edge;
    approximating the anvil assembly and tubular body portion with one another so that an end portion of the first intestinal section, the support structure, and an end portion of the second intestinal section are disposed between the anvil member and the tubular body portion, the support structure being disposed between the first intestinal section and the second intestinal section;
    firing the surgical anastomosis device to sever the portions of the first and second intestinal sections disposed radially inward of the annular knife, and to touch the portions of the first and second intestinal sections radially outward of the annular knife against the structure; and
    expanding the at least one layer of expandable material.

2. The method according to claim 1, wherein:
    the anvil assembly includes a first shaft and a tubular body portion includes a second shaft disposed radially inward of the annular knife, the first shaft of the anvil member being attachable to the second shaft of the tubular body portion; and
    further including the step of attaching the first shaft of the anvil assembly to the second shaft of the tubular body portion prior to the step of approximating the anvil assembly to the tubular body portion.

3. The method according to claim 2, wherein:
    the support structure includes an aperture formed therein; and
    further including the step of inserting one of the first shaft of the anvil assembly and the second shaft of the tubular body portion into the aperture of the support structure prior to the step of attaching the first shaft of the anvil assembly to the second shaft of the tubular body portion.

4. The method according to claim 3, wherein the tubular body portion carries a plurality of surgical staples, the surgical staples being disposed radially outward of the annular knife and wherein in firing the surgical anastomosis device includes deploying the plurality of staples so that the staples penetrate first interstitial section, the support structure and then a second interstitial section.

5. The method according to claim 1, wherein the support structure includes:
    a first and a second membrane extending radially outward from the body.

6. The method according to claim 5, wherein each of the first and second membranes of the support structure is made from a polymeric film.

7. The method according to claim 5, wherein each of the first and second membranes of the support structure is made from polyethylene.

8. The method according to claim 5, wherein each membrane of the support structure includes a first inner layer and a second outer layer.

9. A method of performing a surgical anastomosis procedure, comprising the steps of:
    providing an anastomosis apparatus having an anvil assembly movably mounted with respect to a tubular body portion;
    providing a support structure including a body having an outer terminal edge, and an aperture therethrough, the body being compressible;
    disposing an anvil assembly into a first intestinal section;
    disposing a distal end portion of the surgical stapling apparatus in a second intestinal section;
    positioning the support structure on a shaft of the anvil assembly;
    approximating the anvil assembly and the tubular body portion to capture the body of the support structure between the first intestinal section and the second intestinal section and to compress the body portion therebetween so that a portion of the body extends radially beyond the anvil member and the tubular body portion, at a location between the first and second intestinal sections, and remains substantially uncompressed thereby sealing a radial gap between the first intestinal section and the second intestinal section of the anastomosis site; and
    firing the anastomosis apparatus to join the first intestinal section, support structure, and second intestinal section.

10. The method according to claim 9, wherein the support structure has an unhydrated condition wherein the body has a first diameter and a first thickness, and a hydrated condition wherein the body has a second diameter greater than the first diameter and a second thickness greater than a first thickness.

11. The method according to claim 10, wherein the support structure is premounted onto the shaft of the anvil assembly prior to positioning of the anvil assembly in the first intestinal section, wherein prior to approximating the anvil assembly and the tubular body portion, the method further includes the step of hydrating the support structure to expand the body from the first diameter and the first thickness to a second diameter and a second thickness.

12. The method according to claim 11, wherein the body is constructed from a first part of a multiple-part wound treatment material, and the fluid applied thereto is a second part of the multiple-part wound treatment material.

* * * * *